United States Patent [19]

Kertz

[11] Patent Number: 4,908,315

[45] Date of Patent: Mar. 13, 1990

[54] INTEGUMENT AND METHOD FOR MICROPROPAGATION AND TISSUE CULTURING

[75] Inventor: Malcolm G. Kertz, Missouri City, Tex.

[73] Assignee: Agristar, Inc., Sealy, Tex.

[21] Appl. No.: 21,408

[22] Filed: Mar. 4, 1987

[51] Int. Cl.⁴ .......................... C12N 5/00; C12M 1/16; C12M 1/12; C12M 1/04; A01H 1/00; A01G 9/02

[52] U.S. Cl. ................................ 435/240.4; 435/299; 435/311; 435/313; 47/58; 47/66; 47/84

[58] Field of Search ................... 47/66, 73, 84, 58, 69; 435/240.4, 299, 310, 311, 313

[56] References Cited

U.S. PATENT DOCUMENTS

| | | | |
|---|---|---|---|
| 2,934,204 | 4/1960 | Pardee | 206/46 |
| 2,994,424 | 8/1961 | Selby et al. | 206/46 |
| 3,022,605 | 2/1962 | Reynolds | 47/58 |
| 3,160,986 | 12/1964 | Watson et al. | 47/58 |
| 3,168,887 | 2/1965 | Bodell | 119/3 |
| 3,172,234 | 3/1965 | Eavis | 47/16 |
| 3,256,941 | 6/1966 | Rivman | 229/62 |
| 3,320,697 | 5/1967 | Larsen | 47/34.11 |
| 3,323,640 | 6/1967 | Kugler | 206/47 |
| 3,372,513 | 3/1968 | Shlesinger et al. | 47/58 |
| 3,384,993 | 5/1968 | Kane | 47/58 |
| 3,395,486 | 8/1968 | Campbell et al. | 47/34 |
| 3,524,279 | 9/1967 | Adams | 47/34.13 |
| 3,613,309 | 10/1971 | Coburn | 47/38 |
| 3,739,522 | 6/1973 | Greenbaum | 47/87 |
| 3,824,998 | 7/1974 | Snyder | 128/157 |
| 3,869,828 | 3/1975 | Matsumoto | 47/34.11 |
| 3,941,662 | 3/1976 | Munder et al. | 435/310 |
| 3,971,160 | 7/1976 | Vajtay | 47/34.11 |
| 4,006,561 | 2/1977 | Thoma et al. | 47/58 |
| 4,024,670 | 5/1977 | Stanley | 47/73 |
| 4,034,508 | 7/1977 | Dedolph | 47/84 |
| 4,075,785 | 2/1978 | Jones | 47/64 |
| 4,118,890 | 10/1978 | Shore | 47/28 |
| 4,170,301 | 10/1979 | Jones et al. | 206/423 |
| 4,189,868 | 2/1980 | Tymchuck et al. | 47/84 |
| 4,249,341 | 2/1981 | Huegli | 47/14 |
| 4,251,951 | 2/1981 | Heinstedt | 47/39 |
| 4,400,910 | 8/1983 | Koudstaal et al. | 47/84 |
| 4,407,092 | 10/1983 | Ware | 47/64 |
| 4,424,645 | 1/1984 | Rannali | 47/66 |
| 4,463,522 | 8/1984 | Lindemann | 47/58 |
| 4,562,663 | 1/1986 | Redenbaugh | 47/58 |
| 4,583,320 | 4/1986 | Redenbaugh | 47/57.6 |
| 4,615,833 | 10/1986 | Nelson et al. | 424/84 |

FOREIGN PATENT DOCUMENTS

WO87/00218 10/0887 PCT Int'l Appl. .

OTHER PUBLICATIONS

Jensen et al. 1974, Exper. Cell Res. 84:271–281.
Kybal et al, 1985, Biotechnol. Lett. 7(7):467–470.
J. H. Dobbs and L. W. Roberts, Experiments in Plant Tissue Culture (Cambridge University Press 1982) at Chapter 2, pp. 10–20.
Y. Yamada, "Photosynthetic Potential of Plant Cell Cultures", pp. 89–98, appears in Advances in Biochemical Engineering/Biotechnology (1985).
"Film on the Farm", no author listed; Modern Plastics; Sep. 1956; vol. 34, No. 1, pp. 112–116.

(List continued on next page.)

Primary Examiner—Charles F. Warren
Assistant Examiner—David T. Fox
Attorney, Agent, or Firm—David A. Rose

[57] ABSTRACT

An integument and related process for the micropropagation of tissue is made of a semipermeable, translucent membrane. The integument includes a cellule for completely enclosing and sealing the tissue and growth medium from the ambient environment. Light is transmitted through the translucent membrane to the tissue. The semipermeable membrane allows the mutual penetration by diffusion and osmosis of oxygen and carbon dioxide to permit the tissue to breathe with the ambient environment. The membrane is impermeable to biological contaminants. The integument and related method provides enhanced growth of the tissue and a reduction in contamination.

59 Claims, 4 Drawing Sheets

OTHER PUBLICATIONS

"Gardening with Plastics" by George Taloumis; Horticulture Magazine; Sep. 1953; pp. 369–380, vol. 31, No. 9.

"A New Exposure Model for In Vitro Testing of Effects of Gaseous Pollutants on Mammalian Cells by Means of Gas Diffusion Through Plastic Films" by G. M. Alink, J. C. M. van der Hoeven, F. M. H. Debets, W. S. M. van de Ven, J. H. Koeman and J. S. M. Boleij. Chemosphere No. 2, pp. 63–73; Pergamon Press, Ltd. 1979, Great Britain, "Vertical Bag System Used for Mother Foliage Pot Plants Culture: Effects of Substrates" by O. Marfa, T. Ramos, M. Jover and R. Save, 1986, Acta Horticulturae 178; 245–256, (Unitat de Tecnologia; Agroenergefica, Servei d'Investigation Agraria, Barcelona, Spain).

INTEGUMENT AND METHOD FOR MICROPROPAGATION AND TISSUE CULTURING

FIELD OF THE INVENTION

The present invention relates to a new and improved integument and method for micropropagation and tissue culturing. More particularly, the invention relates to a new and improved integument and method for enhancing tissue growth and decreasing contamination during all stages of the micropropagation of horticultural and agricultural plants.

BACKGROUND OF THE INVENTION

Micropropagation is the process of growing new generation plants from a single piece of tissue that has been excised from a carefully selected parent plant or cultivar This process permits the mass reproduction of plants having certain desirable traits since substantially all of the new generation plants produced are genetically identical to and have all the desirable traits of the parent. The factors considered in selection of parent stock for micropropagation include vigor, growing habits, resistance to disease and insect attack; water, nutrient, temperature, and light requirements. In horticulture, perhaps most important is the quality of the bloom if it is a flowering plant. In agriculture it is more likely that growth rate and yield would be of principal concern.

Tissue culturing is the process of growing cells in vitro and is used to grow both plant and animal cells. Tissue culturing techniques are commonly used in the early stages of the plant micropropagation process where it is desirable to rapidly produce plant cells. The concept of tissue culturing is not new and has its early origins in 1902 from attempts to cultivate cells from leaves. See G. Haverlandt, "Sitz-Ber. Mat.-Nat. Kl. Kais Akad Wiss. Wien III," 69 (1902). Although Haverlandt failed to obtain viable cultures, his work and theory served as a foundation for later attempts by other scientists. The first successful culture of cells was obtained as early as 1934. See R. J. Gautheret, "C.R. Acad. Sci." 198, 2195 (1934).

Plant propagation within the horticulture industry is carried out by one of two general techniques, namely seed propagation or vegetative propagation. Seed propagation is the most common method of plant propagation.

Seed propagation in the past has offered the grower the fastest method of producing plant material. In most plant varieties, large numbers of seed are produced annually, the seeds being easily collected and sown to produce the next generation of plants. Drawbacks to this technique exist. These include yearly fluctuations in seed production, exacting germination requirements, high seedling mortality, and lack of crop uniformity. Lack of uniformity is one of the most significant problems. Seeds are produced by plants according to the genetic variances governed by Mendelian rules. Basically each seed is genetically different and each will grow with its own specific traits.

Vegetative propagation includes three distinct methods: propagation from cuttings, by the division of existing plants, and through micropropagation. Vegetative propagation has offered the grower a degree of crop uniformity that is unattainable through seed propagation, as substantially all the plants produced using any of the three vegetative propagation methods are genetically identical to the parent plant. Thus, vegetative propagation has advantages over seed propagation since plants having certain desirable characteristics can be consistently reproduced. Further, vegetative propagation methods allow for the production of plants that produce little or no viable seed.

There are major drawbacks to the methods of propagation from cuttings and by the division of existing plants. These include the labor intensive operation necessary to produce the new plants and the time to develop a sufficient parent or stock reserve from which to obtain plant material, since each of these two methods requires the removal of relatively large portions of the plant. By contrast, micropropagation eliminates the problems associated with these two forms of vegetative propagation since in micropropagation only very small pieces of tissue are removed from the stock or parent plants. Thus, micropropagation retains the advantages common to all types of vegetative propagation, i.e., identity of progeny and the ability to propagate non-seed producing plants, while having the additional advantage that only a small piece of tissue from the cultivar or parent plant is required.

Despite these advantages over other methods of plant propagation, micropropagation is more commonly used to propagate horticultural strains than agricultural strains because micropropagation of agricultural plants is more time-consuming and costly than seed propagation. Further, plant micropropagation must be carried out under sterile conditions, i.e., in sterile laboratories and culture rooms rather than in the field or greenhouse. Horticultural plants lend themselves to this less efficient method because the plants need not be produced in the massive quantities associated with agriculture, and further, because the consumers—who are purchasing and growing plants as an avocation—are more willing to absorb the higher costs. Nevertheless, micropropagation is increasingly used in agriculture, particularly in the development of new crops.

Although horticulture is primarily an avocation, it is nonetheless important commercially. In fact, gardening is the most popular leisure-time activity, with active participants included in approximately 44% of all households in the United States. See "The National Gardener," Jan. 1987. Excluding food crops and fruit trees, total sales of green plants in the United States in 1985 approximated 25–30 billion dollars.

Improvements in tissue culturing techniques also have applications beyond the micropropagation of plants. Essentially the same culturing process is used to culture animal and even human tissue, such tissue being used in the fields of animal agriculture and human and veterinary medicine.

Micropropagation begins with the selection of a cultivar or parent plant. A cultivar may be selected from existing strains or may be created or developed through such methods as selected breeding and genetic engineering. Researchers are hybridizing plants having individually advantageous traits so as to produce a plant with predetermined characteristics. Further, with the advent of biotechnology, the biologist can transfer desirable genetic material from one plant to another, thus engineering a new plant (genetic engineering). Other genetic manipulations such as protoplast fusion are also being used.

Once the parent plant is selected or achieved through the use of one of the methods described above, micropropagation is used to reproduce the carefully selected or developed plant by means of tissue culturing and cell manipulation.

Great strides are now being made almost daily through genetic engineering and micropropagation via tissue culture. Disease-free clones, germ plasm, accelerated asexual propagation and in vitro propagation are becoming increasingly common in horticulture. Micropagated plants include woody ornamentals, tropicals, and blooming plants. The micropropagation process is a powerful force in the propagation of plant material. It allows mass production of quality plant material in a short period of time and offers definite advantages to both the grower and consumer.

The values of micropropagating plants include:

(1) a means of developing disease-free progeny;

(2) a method of asexual propagation that provides rapid multiplication of selected cultivars;

(3) the preservation of selected varieties (germ plasm); and (4) the development of potentially valuable "sports", naturally occurring mutations.

THE PRIOR ART MICROPROPAGATION PROCESS

The prior art micropropagation process involves four basic stages:
Stage 1 Initial Tissue Culturing
Stage 2 Tissue Culture Multiplication
Stage 3 Differentiation and Plant Formation
Stage 4 Greenhouse Culturing & Hardening

Stage 1—Initial Tissue Culturing

Cultivars or parent plants are maintained under carefully controlled greenhouse conditions in an attempt to yield plant tissue which minimizes the growth of microorganisms and particularly biological contaminants such as viruses, bacteria, fungi, mold, yeast, and single cell algae. After selection of the optimal parent, an area of the plant with meristematic (undifferentiated) tissue is identified and a bulk sample, which includes the meristematic tissue, is removed from the parent. This area is usually where active growth takes place, such as at the tips of stems or at lateral buds.

In plant tissue culturing (or, in any other type of tissue culturing), the main problem is contamination. See J. H. Dobbs & L. W. Roberts, *Experiments in Plant Tissue Culture* (Cambridge University Press 1982) at Chap. 2. Thus, steps must always be taken to insure sterile conditions.

Initially after the bulk sample which contains the meristematic tissue has been removed from the plant, the bulk sample is washed with a mild detergent solution to avoid carrying large soil particles or other ostensible contamination into the laboratory. In the laboratory, any substantial layers of tissue covering the meristematic tissue are removed from the sample. The bulk sample then goes into a 10% sodium hypochloride solution and into a sonicator for 10 to 15 minutes. The sample only is sonicated if it can withstand such treatment. Tissue of certain varieties of plants, such as African violets, gloxinia, and rex begonia for example, could be damaged or destroyed by this sonication process, thus, other known means of sterilization are used for these varieties of plants. The bulk sample is then washed with deionized water, remaining layers of tissue are removed, and the meristematic tissue is exposed and excised by a laboratory technician, often under a stereoscopic microscope. If desired, it can be re-sterilized and re-washed through this same process.

To further prevent the chance of contamination from biological contaminants, the meristematic tissue is excised from the bulk sample under a laminar flow hood which removes airborne contaminants. While still under the hood, the meristematic tissue sample, typically a 0.2 to 1.0 millimeter cube, is transferred into a 150 mm×25 mm test tube containing a suitable growth medium. The media used for the growth medium is an agar-based substance having all the nutrients necessary for tissue growth. One such media which is used is 10 ml of Murashige Minimal Organic Medium manufactured by the Carolina Biological Supply Company.

To also prevent contamination of the culture, the test tube containing the tissue and media must be covered. Typical conventional means for covering the test tube include rubber stoppers and plastic caps. However, because green plants require both carbon dioxide and oxygen to live and grow, means must be provided to allow the tissue within the test tube to exchange gas with the atmosphere. Thus, the test tube and its cover must provide means for such gas exchange. Where a rubber stopper is used, the rubber stopper has a bore therethrough which is tightly packed with cotton. As the growing tissue exchanges gases with the atmosphere, the cotton packing acts as a filter to contaminates such as viruses and bacteria, which may not have been removed from the atmosphere by the laboratory's filtration system. Alternatively, a loosely fitting cap or a cap having baffled slits is used. The loose fit and baffled slits allow the passage of oxygen and carbon dioxide for the required gas exchange.

All working surfaces within the hood are kept clean and sterile. Additionally, the test tubes and covers and the technician's tools are all washed and sterilized in an autoclave prior to the tissue transfer.

The test tubes containing the cultures are then placed in racks in a carefully controlled culture room. Because the ambient atmosphere or environment hosts airborne microorganisms which can pass through the cotton packing, through the baffled slits, or between the loose fitting cap and the side of the test tube to contaminate the new culture, special filtration equipment is required to filter out these airborne contaminants. In addition, the culture room, like the laboratory where the tissue is excised and placed in the cultures, is maintained extremely clean.

In addition, precise temperature, humidity and light conditions must be maintained in the culture room. About 300 to 500 foot-candles of light are required in the culture room. Typically, the culture room is maintained at 80 degrees F. and 80% humidity. It is important to maintain this constant temperature because temperature causes the gases within each test tube to expand or contract. As these temperature changes occur, gases are drawn into and expelled from the test tubes containing the cultures, thereby increasing the risk of contaminations from airborne contaminants which have not been removed by the filtration system. The 80% humidity level is typically maintained in order to prevent the media from drying out through evaporation.

The tissue remains in the media and test tube typically for between 20 and 45 days during Stage 1 depending upon the plant variety being reproduced. During this period, it can be determined whether the culture has been contaminated and the contaminated cultures can be identified and eliminated. Despite the sterile conditions maintained in the laboratory and culture room, many cultures are found to be contaminated during Stage 1 because of surviving microorganisms which were introduced into the culture from the sample of meristematic tissue removed from the parent plant. Once the tissue is established, is growing in the initial culture, and is certified contaminant-free, it may be placed in a Stage 2 culture.

Stage 2—Tissue Culture Multiplication

During Stage 2, the initial tissue culture of Stage 1 is rapidly multiplied by changing the growth medium. Stage 2 growth yields primarily non-differentiated tissue growth.

Having completed Stage 1, the Stage 1 test tubes are carried back to the laminar flow hood from the culture room and sprayed with an alcohol solution to sterilize their outer surface. The tissue grown in Stage 1 is then removed from the test tube and again aseptically transferred in the laboratory under the laminar flow hood to a bottle containing a Stage 2 media. Suitable Stage 2 media include Murashige Shoot Multiplication Mediums A, B, and C, available from the Carolina Biological Supply Company. The bottle, typically the size of a 250 ml Erlinmeyer flask, is then sealed with a cover, often a rubber stopper having an aperture which is heavily packed with cotton and then placed in the culture room. Usually, several tissue samples are cultured in the same Stage 2 bottle, although they may be individually cultured in test tubes as in Stage 1. About 300 to 500 footcandles of light are provided in the culture room.

The growth media used for Stage 2 cultures differs from that used in the initial culturing and includes hormones to induce rapid growth and multiplication of the tissue. The cells in each tissue sample multiply rapidly during Stage 2 to form a cluster of primarily undifferentiated tissue cells, the size of which depends upon the plant variety. The desired cell multiplication takes approximately 20 to 45 days, again depending upon the plant variety. At the end of this period, the tissue samples are removed from the bottle and each is divided into a number of smaller tissue samples, all these steps again being performed in the laboratory under the laminar flow hood. Each resulting tissue sample is then placed back into a clean Stage 2 bottle having fresh media. The bottle is then returned to the culture room. In turn, each culture is grown and divided in a 20 to 45 day cycle. This process and cycle are repeated as often as necessary to obtain the quantity of tissue desired from the cultivar or parent plant.

Stage 3—Differentiation and Plant Formation

During Stage 3, the individual tissue samples grown in Stage 2 are placed in a growth medium which stimulates cell differentiation and the formation and growth of individual plantlets, each plantlet developing roots and foliage. Suitable Stage 3 media includes Murashige Pretransplant Mediums, available from the Carolina Biological Supply Company. Stage 3 prepares the plantlets for greenhouse culture.

During the initial tissue culturing and plant multiplication stages, Stages 1 and 2, the tissue samples were individually grown in small test tubes or grown several to a bottle. In Stage 3, the tissue samples emerging from Stage 2 are planted in larger containers, several per container. Typical containers for Stage 3 growth include a French Square Bottle with a rubber stopper, a G-7 vessel having a specially designed cap as manufactured by the Majenta Corporation, or a baby food bottle with a specially designed cap, as manufactured by the Majenta Corporation, each cover permitting some gas exchange. The plants are still grown in the culture room during this phase of development, but they are placed under increased light conditions so as to promote photosynthesis and growth. The light is increased from 300–500 foot-candles during Stages 1 and 2 to approximately 2000 footcandles during Stage 3. The differentiation and growth process of Stage 3 requires approximately 20 to 45 days depending upon the plant variety.

As the plants grow, roots and foliage intertwine forming a solid mat of plants. Separation of the individual plants for greenhouse culturing and shipping of plants in Stage 4 frequently results in damage to the plants. Some commercial growers will purchase their plants upon completion of this stage. Many, however, will wait until the plants have completed Stage 4, the final production stage. If purchased at the end of Stage 3, the plantlets are removed from the Stage 3 containers and sipped. Upon receipt, since the plantlets have been removed from the sterile environment of the culture room, the commercial grower must immediately remove the plantlets from the shipping containers, rinse them to remove the media in which contaminants can thrive, and then plant immediately.

Stage 4—Greenhouse Culture & Hardening

At Stage 4, the plantlets are removed from the culture room and are transferred to a greenhouse where they are planted individually in small plastic liners which contain a soil medium, typically a presterilized peat moss mix. These liners are placed in a flat (typically 72 liners per flat) where the plants are allowed to grow and mature to shipping size. The greenhouse provides a special environment to harden and prepare the plants for sale to a grower. Depending on the type of plant, most commercial plants remain in the greenhouse 30 to 90 days before they are shipped to the grower in flats.

The plant's tolerance to light must be increased so that the plant can adapt to its natural environment. This process is called "hardening" the plant. The plant's tolerance to light is gradually increased in Stages 3 and 4. During Stage 4, the plants are exposed to up to 8,000 foot-candles in the greenhouse where growth and hardening is to take place. Stage 4 growth normally takes from 30–90 days, depending on the type of plant.

As should be clear, each variety of plant has its own rate of development and growth, and thus, the time periods for each of the four stages of micropropagation will vary accordingly with the plant variety.

While micropropagation has a definite place in the plant propagation world, there are problems associated with the prior art apparatus and process. One of the primary problems is contamination occurring during all stages of plant micropropagation. Any of a wide variety of microorganisms, including Viruses, bacteria, fungus, molds, yeast and single cell algae, can ruin the tissue cultures during the various stages. The smallest of these biological contaminants are the viruses, the largest are the single cell algae. A virus typically ranges in size from 0.1 to 0.45 micrometers although it is suspected that portions of the virus which are as small as 0.01 micrometers may separate from the virus and alone cause contamination. Bacteria typically range in size from 5 to 100 micrometers, while fungi and molds are usually larger than 100 micrometers. Yeast is larger than bacteria, with single cell algae, the largest of these biological contaminants, being larger than yeast.

These contaminants often appear during Stage 1 and typically result from the microorganism being carried along with the meristematic tissue of the parent plant tissue which is introduced into the initial tissue culture. The microorganism introduced into the growing medium reproduces at a much faster rate than the plant cells and produces toxins which soon destroy the plant tissue. Inasmuch as the objective at Stage 1 is to obtain a contaminant-free tissue culture, such contaminated tissue cultures are usually identified and eliminated at this stage and do not threaten the subsequent cultures.

After eliminating such contaminated tissue cultures in Stage 1, any subsequent contamination is usually of airborne derivation. Airborne contamination is often introduced notwithstanding great efforts to eliminate it, efforts which typically include, for example, sterilizing all instruments and containers, carrying out all tissue transfers under sterile conditions while under a laminar flow hood, and even growing Stages 1 to 3 in an aseptic environment with sterile filtered air.

Some contamination from airborne sources results from inherent deficiencies in the containers currently used for the cultures. Typically, Stages 1 and 2 are carried out in test tubes which have close-fitting plastic caps. Alternatively, Stages 1 and 2 are carried out in test tubes or small bottles fitted with rubber stoppers having a bore therethrough, the bore being packed with cotton in an attempt to impede contaminant entry. During Stage 3 the plants are housed is glass bottles with stoppers, the stoppers again having a cotton-stuffed bore formed in its top, or in plastic bottles which have screw or "pop-on" tops. The filtration of the packing material is inconsistent and the fit of the plastic tops and containers varies. Thus, these stages are not carried out in a hermetically sealed environment, which would prevent introduction of air borne contaminants into the cultures, because some gas exchange is needed for tissue and plant growth and life.

Although contamination can enter the cultures from the ambient air in the environment as described above, it is most likely to be introduced when the cultures are transferred from media to media as they proceed through the various micropropagation stages. Contaminants of both airborne and other derivation tend to accumulate on the outer surfaces of the culture containers. During transfer, elimination of these contaminants is attempted by spraying the outer surfaces of the containers with an alcohol solution. However, this will not thoroughly decontaminate the surfaces. Nor will it reach those contaminants which lie under the lip of the caps, or between the rubber stopper and the inner test tube wall. These inaccessible and thus protected contaminants are often carried into and contaminate the next container when the tissue sample is transferred to the next stage.

Another significant disadvantage of the conventional containers is their cost. A rack of forty test tubes with caps can cost up to forty dollars. A single plastic container and top can cost from $1.25 to $1.50. Further, because of its significant initial cost, glassware must be used many times in order to be economically viable. Hence, after each culture, the test tube or bottle must be cleaned and sterilized. Often, even after undergoing the automated sterilization process, the test tubes must be washed by hand to remove especially troublesome accumulations, usually resulting from a contaminated culture. This comprises an extremely time consuming and labor intensive operation.

Additionally, the susceptibility to breakage of glass test tubes and bottles makes them difficult to handle. They are, of course, also expensive to replace. Also, as explained above, the use of the unsealed containers necessitates that the culturing process be carried out in a culture room kept sterile by filtering the air, typically by the employment of expensive HEPA type filters and other sophisticated and costly filtration equipment. The practical problems of plant micropropagation are increased because access to the culture room and laboratory must be carefully controlled to reduce the introduction of contaminants. Persons entering these areas must wear special clothing and surgical masks. Further, as mentioned above, the culture room must usually be kept at 80 degrees F and 80% humidity to prevent temperature gradients, which increase the chance of airborne contaminants entering the culture through the containers, and to prevent the media from drying out. Thus, an inexpensive container which is impermeable to contaminants and which preferably can be thoroughly sterilized (thus affording no "safe havens" to contaminants) and which allows the gas permeability needed for gas exchange, would eliminate many of the disadvantages associated with the conventional containers.

In summary, the prior art sterilized glass or plastic containers such as test tubes, flasks or bottles, utilized in conventional micropropagation technology to grow the tissue and plantlets during the first three stages, have serious drawbacks. Since glass permits no gaseous interchange through its walls, the rubber stopper having cotton packing or some similar filter, a loosely fitting cap, or a baffled plastic cap must be employed to allow an adequate exchange of gas between the tissue or plant and the ambient atmosphere and environment. Such devices restrict the amount and rate of gas which can be exchanged. Further, such caps and stoppers do not totally protect the plant from contamination by microorganisms such as viruses, bacteria and fungi. Thus, it is of paramount importance that the tissue culture room and laboratory be kept extremely clean and their atmospheres filtered. Further, precise temperature, humidity, and light conditions must be maintained in the culture room. The original cost of the glass containers; the labor and equipment cost to maintain the sterility of the containers; and the added cost of the facilities, equipment, and related conditions required to maintain a sterile growing environment, all represent major cost factors associated with the use of such containers in conventional plant micropropagation process.

A recent study, in which other studies are cited, reports that certain factors are known to affect the growth rate of plant cells in tissue culture. See Y. Yamada, "Photosynthetic Potential of Plant Cell Cultures," appearing in A. Fletcher "Advances in Biochemical Engineering/Biotechnology" (1985) at page 89. These factors include the amounts of Auxins, cytokinins, sugars, and inorganic nutrients, as well as the ambient temperature and gas phase. This recent study, however, does not mention that increasing the rate of gas exchange will enhance cell or plantlet growth. The discovery that increasing gas exchange enhances tissue culture and plantlet growth is, therefore, a significant departure from the teachings of the prior art.

The present invention overcomes many of the deficiencies of the prior art techniques of micropropagation and tissue culturing by having the following advantages:

(1) enhanced protection from contamination;
(2) increased growth rates;
(3) no requirement for a sterile culture room;
(4) no requirement for expensive glass containers or the incurrence of replacement costs due to breakage;
(5) no labor cost associated with cleaning and sterilizing containers for reuse;
(6) an increase in the number of plantlets from a culture;
(7) a reduction by approximately one-half the amount of media required in each culture;
(8) the elimination of the requirement of strict humidity control in the culture room;
(9) an increase in the number of cultures which can be produced in the same size culture room;
(10) a reduction in the size of the media preparation area and in the size of the autoclave; and
(11) an increase in the number of new cultures which can be established by a laboratory technician.

Other objects and advantages of the invention will appear from the following description.

SUMMARY OF THE INVENTION

The present invention includes a new integument and related process for micropropagation. The integument is made of a semipermeable and translucent membrane which allows light transmission and gas exchange but seals out the biological contaminants in the ambient environment. The membrane forms a plurality of cellules which contain the tissue sample and media. The cellule is sealed so as to completely enclose and seal off the tissue. The membrane is perferably a high density polyethylene material. A new and improved envelope is provided for growing the plantlet in a soil medium. Further, a support suspends the integuments and envelopes within the culture room and greenhouse to conserve space.

One of the principal advantages of the present invention is that biological contaminants cannot penetrate the membrane of the integument, and thereby contaminate the culture. Yet, the semipermeable membrane ensures enhanced gas exchange, gas exchange being necessary for tissue growth and plant life. Because the integuments are contaminant impermeable, tissue cultures contained therein need not be cultured in a sterile environment, and the costs and problems associated therewith are eliminated.

The integument of the present invention is also liquid impermeable so that the media, typically a liquid or semi-solid which sustains the tissue or plant's growth while in the integument, cannot escape and dry out. Thus, using the present invention, it is not necessary to maintain a precise humidity level in the culture room which would again require special and costly equipment.

A completely unexpected benefit of using the semipermeable integument is that the tissue and plantlet growth rates are dramatically increased. This increase is believed to occur because oxygen and carbon dioxide, which are needed for respiration and photosynthesis, are available in greater quantities than when the process is carried out in prior art glass and plastic containers where the rubber stoppers, caps and filters, which are required to prevent the entrance of contaminants, impede gas exchange.

A preferred embodiment of this integument is formed from heat sealed high density polyethylene. This material has been found impermeable to contaminants and, because it is completely sealed once the tissue sample is in place, the entire outer surface can be thoroughly decontaminated by emersion prior to tissue transfer. There are virtually no areas where contaminants can accumulate and avoid decontamination.

With the preferred embodiment of the invention, the costs of micropropagaion are greatly reduced since the cost of the integument of the present invention is much less than the cost of prior art containers. To produce the number of integuments of the present invention, which would be equivalent to a rack of forty test tubes, will cost less than twenty five cents, as compared with forty dollars for the test tubes. The preferred integuments are, unlike glass test tubes, essentially unbreakable. Their low cost makes them completely disposable, eliminating the costs associated with washing and the often-less-s-than sterile product which results.

The apparatus of the invention has other applications other than the tissue culturing stages of micropropagation. For example, improvements in growth rates were observed when the integuments were used in growing plants from seeds.

BRIEF DESCRIPTION OF THE DRAWINGS

For a detailed description of a preferred embodiment of the invention, reference will now be made to the accompanying drawings, wherein.

DESCRIPTION OF THE PREFERRED EMBODIMENT

Figure 1:
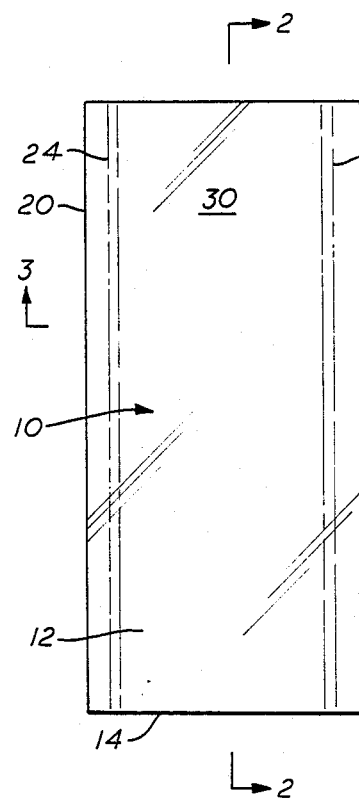
FIG. 1 depicts a frontal view of the integument of the present invention.
Figures 2, 3:
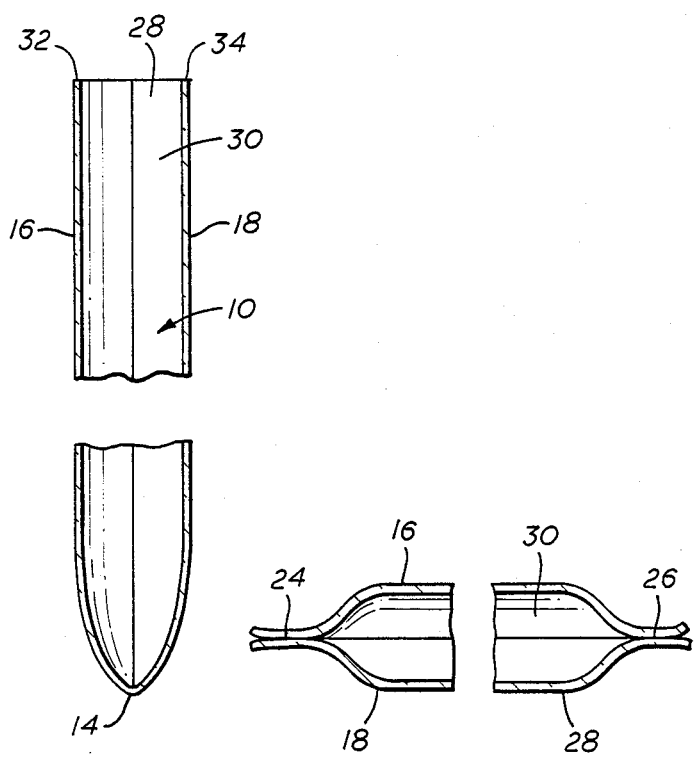
FIG. 2 depicts a partial elevation cross-sectional view of the integument of FIG. 1 taken along line 2—2 as shown in FIG. 1 with the material of the integument enlarged.
FIG. 3 depicts a partial top view of the integument of FIG. 1 with the material of the integument enlarged.

Referring initially to FIGS. 1, 2 and 3, there is shown the integument 10 of the present invention for enclosing in a membrane 12 the plant tissue from a parent plant or cultivar during the first three stages of micropropagation. When sealed, the membrane 12 completely and entirely surrounds and encloses the tissue from the ambient environment.

The integument 10 is made by folding membrane 12 over at 14 such that two sides 16, 18 are formed. Sides 16, 18 are heat sealed at 24, 26 along the entire length thereof and adjacent to longitudinal edges 20, 22 of membrane 12 so as to form an envelope. The envelope shaped integument 10 includes a cellule 30 forming an expandable chamber for containing the plant tissue and growth medium. The cellule 30 has an approximate average volume of 50 ml for most varieties of plants. As can be appreciated, the size and volume of the chamber of cellule 30 can be varied to host the particular tissue or plantlet contained therein. Thus, cellule 30 may be of various sizes. The cellule 30 has at least initially, an open end 28 formed by the terminal edges 32, 34 of membrane 12. End 28 serves as a port of entry of cellule 30 for receiving the plant tissue and media. As can also be appreciated, rather than being made of a single folded membrane 12, integument 10 may be made of two individual and separate pieces of material such as a base material and a frontal material. In this embodiment, the bottom of cellule 30 is formed by heat sealing the frontal material to the base material near the lower terminal edges thereof as distinguished from the fold at 14 where a single piece of material is used as described with respect to FIGS. 1–3.

The membrane 12 is a polyethylene material which is pliable and collapsible such that it can be stored and shipped in rolls. Further, the polyethylene is so inexpensive as to be disposable upon completion of any particular stage of the micropropagation process. Preferably, the membrane 12 is made of high density polyethylene.

Figure 4:
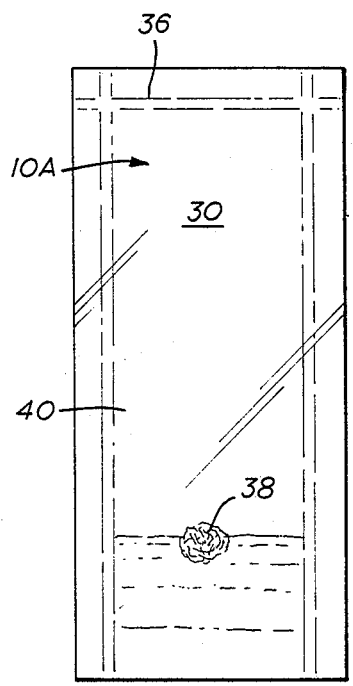
FIG. 4 depicts a meristematic tissue sample being cultured in the integument of FIG. 1.
Figure 5:
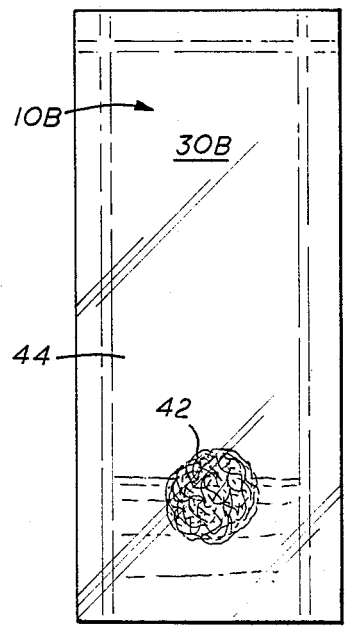
FIG. 5 depicts the initial tissue culture from Stage 1 being multiplied during Stage 2 in a new integument of FIG. 1.
Figure 6:
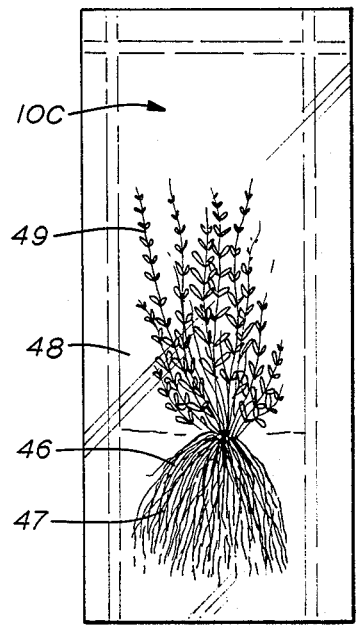
FIG. 6 depicts the growth of an individual plantlet during Stage 3 in a new integument of FIG. 1.

Referring now to FIGS. 4 to 6, the integument 10 is shown in each of the first three stages of micropropagation. As is shown, after the plant tissue and media have been received by cellule 30, the port of entry at open end 28 is heat sealed at 36 along the entire length thereof and adjacent to the terminal edges 32, 34 of membrane 12 to close and seal cellule 30 containing the plant tissue and media therein. At this time the plant tissue is completely and entirely encapsulated from the ambient environment and sealed from biological contaminants in the ambient environment. FIGS. 4 to 6 schematically illustrate the integuments 10A, B and C investing the plant tissue and media in each of the first three stages of micropropagation. FIG. 4 depicts the meristematic tissue 38 from a parent plant or cultivar invested within integument 10A together with suitable media 40 such as Murashige Minimal Organic Medium manufactured by Carolina Biological Supply Company. FIG. 5 illustrates the use of another integument 10B during the second stage of tissue culturing. The initial tissue culture 42 from Stage 1, or a portion of such tissue, is transferred to cellule 30B containing a suitable Stage 2 medium 44 such as Murashige Shoot Multiplication Mediums A, B and C manufactured by Carolina Biological Supply Company. FIG. 6 shows an individual plantlet 46 grown in Stage 2 enclosed by another integument 10C and placed in a medium 48 such as Murashige Pretransplant Medium manufactured by Carolina Biological Supply Company to stimulate cell differentiation and the growth of individual plantlets such as 46, each plantlet 46 developing roots 47 and foliage 49.

Figure 7:
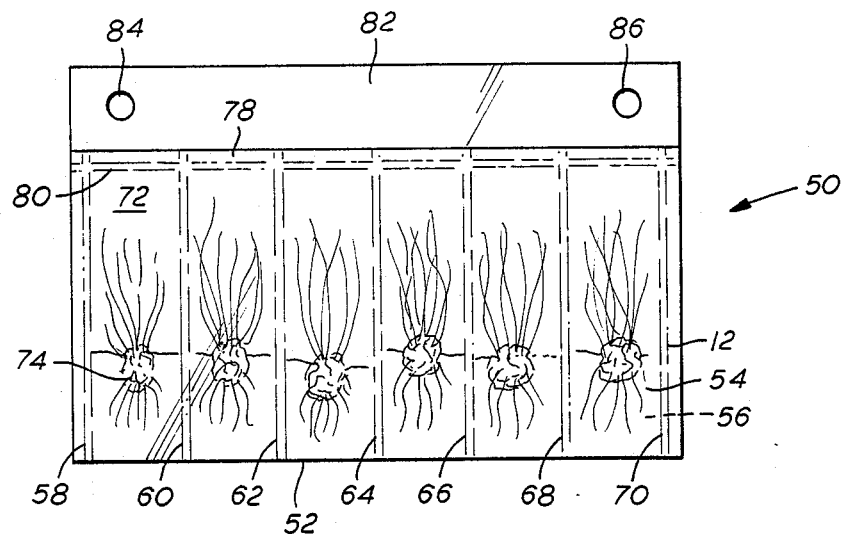
FIG. 7 depicts an integument pack with individual cellules of the type shown in FIG. 1.

Although the integument 10 has been shown and described as providing a single cellule 30 for enveloping an individual tissue, it is preferred that the integument form a plurality of cellules. Referring now to FIG. 7, there is shown an integument pack 50. Integument pack 50 is made of membrane 12 and is formed similarly to integument 10 of FIG. 1. For most applications, the integument pack 50 has dimensions of approximately 12 inches wide and 6 inches high. Integument pack 50 is formed by folding membrane 12 over at 52 so as to form sides 54, 56. As distinguished from integument 10, sides 54, 56 are heat sealed along the entire longitudinal length thereof at 58, 60, 62, 64, 66, 68 and 70 to form six individual cellules 72. Individual tissue samples 74 and media 76 are shown invested in each of the cellules 72. The plant tissue and media may be for any of the first three stages of micropropagation as represented in FIGS. 4 to 6. The ports of entry at the upper end 78 have been heat sealed at 80 along the entire length of integument pack 50 to close cellules 72 after the tissue 74 and media 76 are inserted into the cellules 72. An upper flap or band 82 may be formed at the upper ends 78 of membrane 12 for the purpose of suspending integument pack 50 in the vertical position. Suitable connection means such as apertures 84, 86 may be provided through band 80 for attachment means such as drapery hooks or S-hooks to suspend integument pack 50 vertically.

Figure 16:
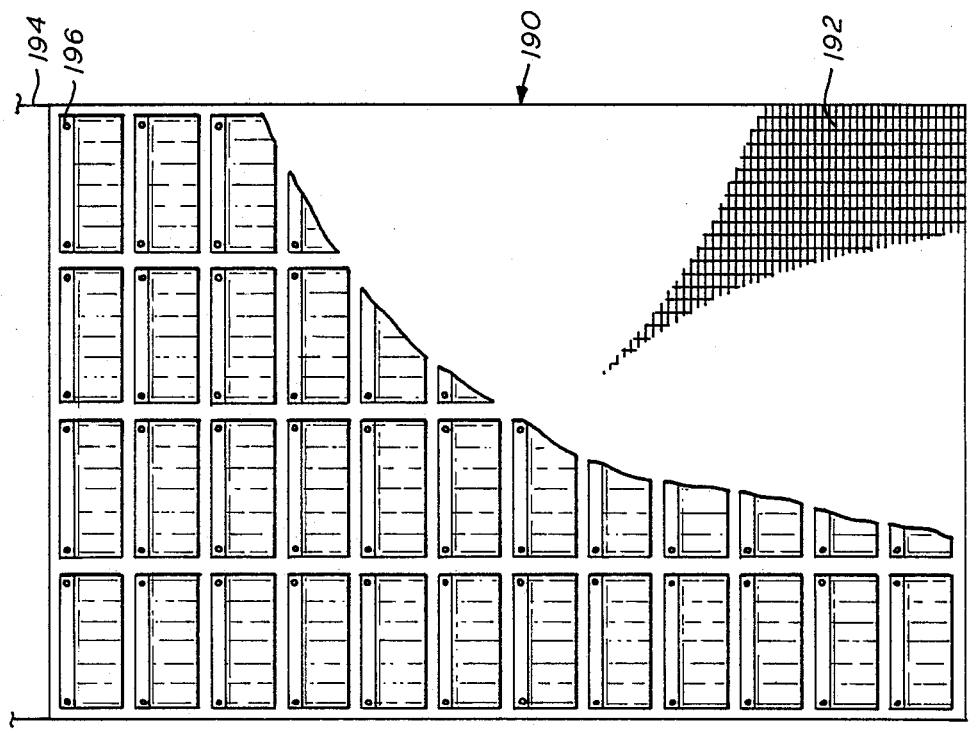
FIG. 16 depicts a frontal view of a rack for supporting an array of integument packs and envelopes.
Figure 15:
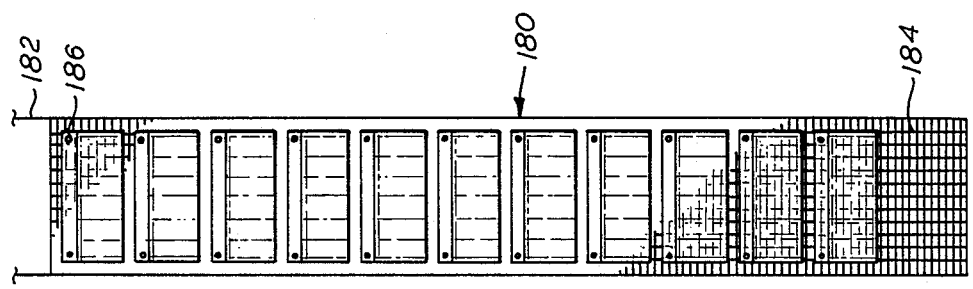
FIG. 15 depicts a frontal view of a standard for supporting a plurality of integument packs and envelopes.

Referring now to FIGS. 15 and 16, suspension means are shown for suspending the integument packs 50 within the laboratory, culture room, greenhouse, or other growing area where the tissue cultures, plantlets or plants are housed and stored during micropropagation. FIG. 15 shows a standard 180 for supporting a plurality of integument packs 50. The number of integument packs 50 which are suspended is only limited by the height of the storage room, the amount of light available, and the size and density of the plant. In many typical such conditions, the standard 180 will have dimensions of six feet high and 1 foot wide and will include twelve locations for integument packs 50 to be attached to or suspended from the standard 180. Integument packs 50 are normally 6 inches high. The lowest location, number 12, is shown empty of integument packs 50 in FIG. 15 for purposes of illustrating support 180. One location can support a plurality of integument packs 50, and often five integument packs 50 are suspended at one location on the standard 180 to provide further space savings.

Standard 180 may be any vertical support held upright within the growing area. Generally the standard 180 is suspended within the growing area such as by chain or cable 182. Standard 180 is preferably a one foot by six foot piece of one inch by two inch heavy gauge wire mesh 184 such as is used for wire fences. The mesh grid may be of any size to conveniently suspend the desired number of integument packs and must not be so fine a mesh grid as to block available light. A solid standard such as wood would be undesirable since wood is opaque to light and would inhibit air movement within the storage area.

Individual integument packs 50 are attached to the standard 180 by attachment means such as hooks 186 inserted into apertures 84, 86 and engaging one of the mesh wires of standard 180. The membrane 12 of integument pack 50 is preferably of high density polyethylene which has sufficient strength that the integument packs 50 can be suspended directly from apertures 84, 86 without the need of grommets or other such reinforcements. Appropriate means such as labels may also be provided on standard 180 for identifying the plant tissue growing within individual integument packs 50 suspended on a particular standard 180.

FIG. 16 shows a rack 190 supporting an array of columns and rows of integument packs 50. As shown, rack 190 is 4 feet by 6 feet in size and supports four columns and twelve rows of integument packs 150. The array size may be varied for the same reasons as those described for varying the size of standard 180. Rack 190 also is similar to standard 180 in design and purpose. Rack 190 is preferably made of wire mesh 192 having suspension means 194 for suspension within the growing area. Individual integument packs 50 are suspended on rack 190 by attachment means 196.

Suspending the growing tissue and plants vertically at different elevations markedly reduces the amount of space required in the growing areas, such as culture rooms or greenhouses. The suspension of plant tissues and plantlets above other plant tissues and plantlets is allowed because of the translucency of integument packs 50 and the minimum light blockage of the wire mesh of standard 180 and rack 190. Where the light source is located above the standards 180 and racks 190, light is able to pass through the integument packs 50 suspended in the upper rows to reach the tissue and plants growing in the integument packs 50 in the lower rows. Although the lower rows do not receive as much light as the upper rows, the light is still sufficient to sustain the hardy growth of the tissues and plants in the lower rows. Further, those plants requiring the most light may be located in the upper rows, with those plants requiring shade or reduced light placed in the lower rows. Likewise, if the light source is to one side, the light can pass through one rack of integuments to reach other adjacent racks.

The suspension of standards 180 and racks 190, in most growing area layouts, will also enhance air movement within the growing area between the tissue cultures and plants stored therein. Many conventional growing area layouts concentrate the tissue cultures or plants at a given elevation within the growing area, such as on countertops or working surfaces, such that there is a limited movement of air between the plants. The standards 180 and racks 190 prevent the occurrence of a dead air space adjacent the plant tissues and plantlets housed within the growing areas.

Thus, by increasing light transmission and the availability of air for gas exchange through the suspension of integument packs 50 on standards 180 and racks 190, growth of the tissue and plants is enhanced and the growing area requirements are reduced.

The cellule, and thus the integument, is sized in accordance with the plant tissue or plantlet to be grown. Referring now to FIGS. 9 to 14, there is shown another embodiment of the integument shown in FIGS. 1 and 7 that is adapted and sized for the micropropagation of lettuce, spinach or other leafy vegetables. The integument 90 for enclosing the tissue for a leafy vegetable is made of a membrane 92, membrane 92 being like that of membrane 12 for integument 10 or integument pack 50 as shown in FIGS. 1 and 7 respectively.

Figure 14:
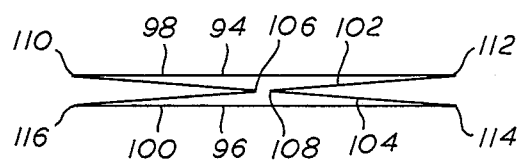
FIG. 14 depicts a top view of the integument shown in FIG. 13.
Figure 10:
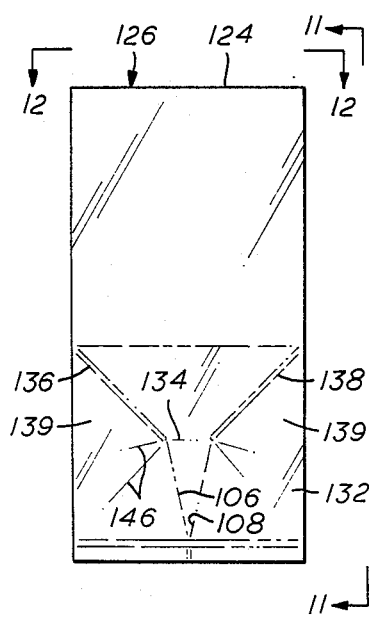
FIG. 10 depicts a front elevation view of the integument of FIG. 9 in the open position.
Figure 13:
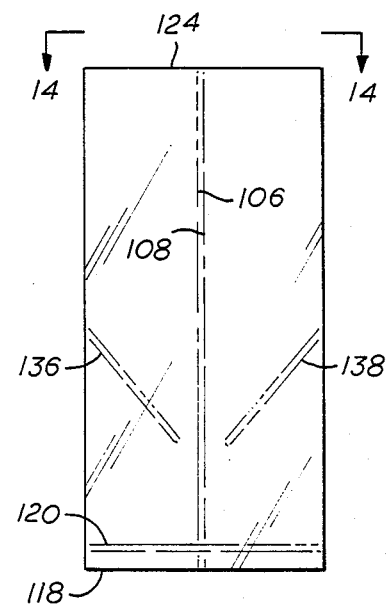
FIG. 13 depicts a front elevation view of the integument of FIG. 9 in the folded position.

Integument 90 is made by membrane 92 being extruded in tubular form having a circumference of approximately 24 inches. The tubular membrane 92 is folded into quarter panels 94, 95, 96, 97 and one eighth panels 98, 100 and 102, 104, best shown in FIGS. 9, 12 and 14. One eighth panels 98, 100 and 102, 104 are formed by folding quarter panels 95 and 97 at 106 and 108, respectively. Quarter panels 94, 95, 96 and 97 were formed by folding tubular membrane 92 into quarter lengths, at folds 110, 112, 114, 116. Folds 106, 108 are directed inwardly as shown in FIG. 14 and one end 118 of tubular membrane 92 is heat sealed at 120 in the folded position as shown in FIG. 13 to produce a cellule 122 to house the leafy vegetable tissue and media. The cellule 122 has a volume of approximately 1000 ml which can be varied according to the particular leafy vegetable plant tissue grown therein. The other end 124 of tubular membrane 92 is initially left open as a port of entry 126 to receive the leafy vegetable tissue and media.

Figure 11:
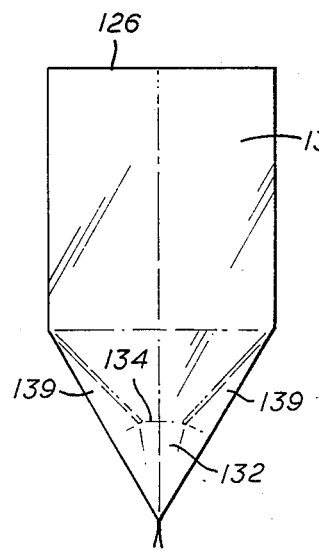
FIG. 11 depicts a side elevation view of the integument of FIG. 10 in the open position.

Cellule 122 preferably includes a foliage chamber 130 and a root chamber 132 with an open neck 134 therebetween, best shown in FIG. 11. Chambers 130, 132 and neck 134 are formed by heat sealing portions of one eighth panels 100 and 104 to quarter panel 96 at 136 and 138 and by heat sealing portions of one eighth panels 98 and 102 to quarter panel 94 at 140 and 142. Additionally, upon expanding integument 90, heat seals 136, 138 and 140, 142 create creases at 106, 108 and 146 shown in FIGS. 9 and 10 to form root chamber 132.

The foliage chamber 130 and root chamber 132 of cellule 122 permit a separation of the foliage from the root system during growth and more particularly to separate the foliage from the media. A plantlet is positioned within cellule 122 such that the foliage grows within foliage chamber 130 and the root system extends from the foliage chamber 130 down through neck 134 and into the root chamber 132 where the media is disposed. Given a cellule 122 with a volume of approximately 1000 ml, the root chamber 132 is sized to contain approximately 50 ml of media. By maintaining the integument 92 in the vertical position, all media will flow downward into root chamber 132. This downward flow is facilitated by the angular heat sealing at 136 and 138. Thus, the media is thereby kept separate from the foliage. This permits the foliage to be kept clean of media and to permit the leafy vegetable to grow in a preferred and desirable symmetric shape. Without the division of cellule 122 into a foliage and a root chamber, the leafy vegetable would grow in a haphazard form losing its symmetry. Further, with the reduced neck portion 134 separating cellule 122 into a root chamber 132 and foliage chamber 130, the media is retained in the root chamber 132 and its flow into the foliage chamber 130 is prevented or retarded when the integument 90 is tipped or inverted since the media will tend to flow into the upper angular portions 139 of root chamber 132 instead of flowing through neck portion 132. Additionally, the reduced neck portion 134 tends to secure a mature plant in position within cellule 122 since the plant's roots will grow into a mass having a size larger than the cross sectional area of neck portion 134. This growth of root mass also acts to impede the flow of media into the foliage chamber 130.

The material for membrane 12 of integuments 10, 50 and for membrane 92 of integument 90 is critical to providing the desired environment for the tissue and plantlet during the first three stages of micropropagation and in particular enhancing growth by permitting optimum gas exchange and light transmission. Gas exchange, for example, is needed for the necessary biochemical actions required for plant growth. Understanding the role of the gases and gas exchange requires an explanation of the utilization of each gas individually.

Two functions of green plant growth are photosynthesis and respiration. Photosynthesis is the biochemical process where green plants convert carbon dioxide and water into complex carbohydrates in the presence of light of a given wave length and intensity for a given period of time. The process is affected by a number of environmental factors including quality of light, availability of water, availability of carbon dioxide, temperature, leaf age and chlorophyll content of the tissue. Photosynthesis is also referred to as a carbon dioxide fixation. The exact chemistry of the process is complex but in essence, chlorophyll in the presence of carbon dioxide, water and light converts the carbon dioxide and water into complex carbohydrates that are in turn converted into sugars and utilized by the plant as a food source.

One of the by-products of this process is the production of free oxygen. Fixation of carbon dioxide by plants accounts for a large portion of their carbon content and subsequent weight increase during growth. The exact uptake of carbon dioxide by plants varies from species to species. However, a range between eight and eighty milligrams of carbon dioxide per hour for 100 cubic centimeters of tissue surface can be used as an approximation of the carbon dioxide intake for most plants exposed to good environmental conditions. This intake can be directly related to the dry weight of plant tissue. At an uptake rate of 25 milligrams of carbon dioxide per hour for 100 cubic centimeters of tissue surface, an increase of 5% of the original weight of the tissue can be realized in a one hour period. From this overview of photosynthesis and carbon dioxide fixation, it is clear that among the critical factors affecting plant growth is the availability of carbon dioxide.

The other function relating to the gases of interest is respiration. This process is essentially an oxidation reduction reaction where oxygen serves as the oxidizer to the carbohydrates and sugars formed during the process of photosynthesis. Again, the exact chemistry involved is very complicated. However, the end result is a release of chemical energy necessary for continued growth of the plant. As in photosynthesis, or carbon dioxide fixation, a number of environmental factors affect the uptake of oxygen for the respiratory process. These include temperature, light, tissue starvation, availability of oxygen and tissue age. While respiration is believed to take place at all times in plant tissue, there is a noted increase in this activity in the absence of light. This is believed to be a result of the decreased creb cycle activity in the absence of light.

Oxygen uptake for use in respiration varies from species to species and while no generally accepted range has been established for plants in ideal environmental conditions, uptake of up to 350 microliters to 1,480 microliters per gram of fresh tissue has been recorded. There has been no direct correlation of fresh weight to oxygen uptake. There is also a difference in oxygen uptake from tissue to tissue within a given plant. Woody tissue and starch storage organs have the lowest uptake, while root tips and other regions containing meristematic cells have the highest uptake rate. This can be directly related to the activity of growth in a given area of the plant where the most active areas require the greatest energy production and consume the greatest amount of oxygen. From this, it is clearly defined that the presence of available carbon dioxide and oxygen is essential to the continued growth of green plant tissue.

In prior art micropropagation procedures, the exchange of oxygen and carbon dioxide between the plant tissue disposed within a glass or plastic container for protection from contamination has been severely limited in that the gas exchange must take place through the cotton packing disposed in the bore of the rubber stopper, between the loose fit of the top and the container and a plastic lid or top, or through the slits in the baffled plastic top. This curtailment of gas exchange has limited the growth of the plant tissue. The material of membranes 12, 92 provides a marked enhancement of permitted gas exchange as compared to the prior art glass or plastic containers.

The membranes 12, 92 are made of a translucent and semipermeable material. The preferred material is a high density polyethylene, material no. 9650T, lot no. T011235 manufactured by the Chevron Chemical Company of Orange, Tex. It has a permeability to water vapor of 0.32 grams per 100 square inches per 24 hours for a sheet which is 1.25 mil in thickness. It is preferred that the material of membrane 12, 92 have a thickness of 1.25 mils. Other materials which have the desired light translucency, gas permeability and contaminant impermeability are also available for membranes 12, 92. The high density polyethylene at a thickness of 1.25 mils forms a molecular structure during the extrusion process which is especially useful as a membrane for integuments. The high density polyethylene is made from linear crystalline polymers of suitable molecular weight with high tensile strength and extension modulus, a high degree of symmetry, strong intermolecular forces and a controlled degree of cross-linking between layers. The cross-links between adjacent layers of polymers are introduced to prevent the polymeric chains from slipping under applied stress. The lightly cross-linked adjacent uniform layers of polymers of the high density polyethylene for membranes 12, 92 form interstices therebetween which allow the preferred diffusion and osmosis therethrough for the desirable gas exchange and light transmission between the ambient environment and the plant tissue. These interstices are smaller than 0.01 micrometers so as to preclude the passage therethrough of even the smallest microorganisms, such as viruses, which can contaminate the tissue. It also provides rigidity to facilitate the transfer and handling of the cultures. Upon sealing off the cellule, the tissue is completely enveloped and enclosed from the ambient atmosphere and environment, as distinguished from prior art containers, so as to prevent any introduction of contaminants.

The necessary gas exchange between the plant and the atmosphere of the ambient environment due to the production of the by-product oxygen by the plant during photosynthesis and the oxygen uptake of the plant during respiration takes place by osmosis. The gases diffuse or propagate through the semipermeable membrane 12, 92, which separates the miscible gases in the ambient atmosphere and within the cellule, in moving to equalize their concentrations. The osmotic pressure or unbalanced pressure between the ambient atmosphere and cellule gives rise to the diffusion and osmosis causing an interaction or interchange of gases by mutual gas penetration through the separating semipermeable membrane 12, 92. Thus, the inventive membrane of the integument permits the tissue to breathe by osmosis and air to diffuse through the semipermeable membrane and yet prevent the passage of biological contaminants.

The material of membranes 12, 92 is translucent and allows the passage and diffusion therethrough of light rays having at least the wavelengths of 400 to 750 nanometers. Individual wavelengths of light in the range of 400 to 750 nanometers are required by individual photosynthetic agents, such as the chlorophylls, in green tissue plants to provide the reactions necessary for life and growth. The reduced thickness of the material for membranes 12, 92 and the uniformity of molecular structure formed in part by the extrusion process for the material for membranes 12, 92 permits greater light transmission to the tissue sample enclosed by the integuments than has previously been allowed by the glass and plastic of prior art containers. The approximate 1.25 mil thickness of the material for membrane 12, 92 as compared to the much thicker prior art glass or plastic containers, substantially enhances the amount of light and the various individual wavelengths of light which are received by the tissue culture. It is important that each wavelength of light necessary for each photosynthetic agent to react pass through the integument. The uniformity and light cross-linking of the molecular structure of the material for membranes 12, 92 provides a pathway of lesser resistance for light. The molecular structure of glass and plastic of the prior art containers is more complicated and thus creates a more complex pathway through the glass or plastic through which the light must pass to ultimately reach the plant tissue. Thus the thicker and more complex molecular structure of the prior art glass and plastic containers inhibits light passage and may filter out certain wavelengths of light necessary for the photosynthetic agents of green tissue plants.

The new and improved integument of the present invention permits the utilization of a new and improved process for micropropagation. This process includes four stages as hereinafter described.

Stage 1: Initial Tissue Culturing

The cultivars or parent plants to be micropropagated are maintained under carefully controlled greenhouse conditions in an attempt to yield plant tissue which minimizes the growth of microorganisms and particularly any biological contaminants. After selection of the optimal parent, an area of the plant with meristematic (undifferentiated) tissue is identified, and a bulk sample, which includes the meristematic tissue, is removed from the parent plant. This area is usually where active growth takes place, such as at the tips of stems or at lateral buds (between the leaf apex and the connection to the stem).

To prevent contamination of the culture by biological contaminants, the meristematic tissue is excised from the bulk sample and transferred to the growing medium under a laminar flow hood which removes airborne contaminants. Prior to the placement of the meristematic tissue sample into cellules 72 of integument pack 50, five ml of a suitable media (as distinguished from 10 ml in the prior art tissue culturing process) such as Murashige Minimal Organic Medium manufactured by Carolina Biological Supply Company is inserted into cellules 72. This medium is an agar-based substance containing all the required nutrients for tissue growth. Integument pack 50, containing the media therein, is then rolled and sterilized in an autoclave. This procedure tends to close the open upper side 78 of cellules 72. See FIG. 7. Later, under the laminar flow hood, the integument packs 50 are unrolled and its cellules 72 opened one at a time prior to tissue placement. A meristematic tissue sample, typically a 0.2 to 1.0 mm cube, is then placed into an individual cellule 72 of integument pack 50, a single cellule being shown in FIG. 4.

After tissue placement, the ports of entry into cellules 72 again tend to immediately close, reducing the length of time that the samples are exposed to the environment and that contaminants can enter. Thereafter, the upper ends 78 of cellules 72 are heat sealed at 80, thereby forming a complete investment and envelope around the plant tissue. In this state, the plant tissue is completely impermeable to contaminants as distinguished from the prior art containers.

Less media is required in the present inventive process because in the integument, the media tends to flow up the inner walls of the high density polyethylene and thereby more completely engulf the tissue sample. In addition, the membrane of the preferred embodiment tends to prevent the media from drying out, as distinguished from the use of the prior art containers.

The integument packs 50 are then suspended on a suitable rack by means of hooks and suspension means 84, 86 for a sufficient period of days to determine whether the tissue culture is contaminant-free. The integument packs 50 are exposed to approximately 300–500 foot-candles of light during this first stage.

Using the present inventive process, precise temperature and humidity conditions need not be maintained in the culture room. In the prior art process, as temperature changes occurred, atmosphere would be drawn into and expelled around the tops of the glass containers containing the tissue cultures, thereby increasing the risk of contaminations from airborne contaminants which had not been removed by the prior art air filtration system. Further, the 80% humidity level was typically maintained in the prior art in order to prevent the media from drying out through evaporation. Such is not critical in the inventive process. Furthermore, and importantly, the inventive process, as distinguished from the prior art process, can be carried out in an environment which does not require a sterile, filtered air-flow since each cellule 72 of the integument pack 50 is contaminant impermeable.

Once the tissue culture has been established, and it is growing in the initial culture and has been certified contaminant-free, it is ready for Stage 2.

Stage 2: Tissue Culture Multiplication

During Stage 2, the initial tissue culture resulting from Stage 1 is multiplied. Under the laminar flow hood, the cellules 72 of the integument packs 50 of Stage 1 are opened with a sharp sterilized knife and the tissue samples, or portions thereof, are transferred to a second set of unused integument packs 50, an individual integument pack being shown in FIG. 7. Multiplication of the tissue culture occurs by using a different media. The media used for Stage 2 cultures differs from that used in Stage 1 culturing and includes hormones to induce rapid growth and multiplication of the tissue. Suitable Stage 2 media include Murashige Shoot Multiplication Mediums A, B, and C, available from the Carolina Biological Supply Company. Again, only 5 ml of media are required as compared to the 10 ml in the conventional prior art process. The integument packs 50 of Stage 2 are then heat sealed and suitably disposed on a rack within a culture room. About 300 to 500 footcandles of light are provided. During this period, Stage 2 growth yields primarily non-differentiated tissue growth. The cells in each tissue sample multiply rapidly during Stage 2 to form a cluster of primarily undifferentiated tissue cells, the size of which depends upon the plant variety. The desired cell multiplication takes approximately 20 to 45 days, again depending upon the plant variety.

After each Stage 2 cycle, the integument packs containing the cultures are immersed in a solution of sodium hypochloride, rinsed, returned to the laminar flow hood, opened, and the tissue is removed. The tissue is then subdivided by cutting into a number of small pieces, each of which will then be cultured. Each time the tissue samples are divided, the individual smaller tissue samples are inserted into cellules 72 of unused integument packs 50. All of these steps are performed in the laboratory under a laminar flow hood.

Each culture is grown and divided in a 20 to 45 day cycle until a sufficient number of tissue samples have been produced to meet production goals. As an example, if each tissue culture emerging from Stage 1 produces a cluster of tissue which in turn yields five tissue samples capable of culturing, over 15,000 cultures will have been produced at the end of seven months of Stage 2 multiplication. With the exception of a few naturally occurring mutations or "sports," each of these resulting cultures of Stage 2 can then be grown into an individual plant which will be genetically identical to the parent plant. Thus, when the desired number of cultures have been produced in Stage 2, the tissue cultures then are ready for Stage 3 production.

Stage 3: Differentiation and Plant Formation

During Stage 3, the cellules 72 of the integument packs 50 of Stage 2 are opened and tissue samples therein are divided and transferred to a third set of unused integument packs 50 as shown in FIG. 7. Although a single plant tissue growing into a plantlet is shown disposed within each individual cellule 72 in FIG. 7, during Stage 3, a plurality of plant tissues may be disposed within an individual cellule if desired. This may be done to save additional space. However, in the inventive process, the plantlets may be grown separately in the new integument packs 50, eliminating the need for plant separation and the damage associated with untangling roots and foliage of several individual plants.

During Stage 3, the individual tissue samples grown in Stage 2 are placed in a media which stimulates cell differentiation and the growth of individual plantlets, each plantlet developing roots and foliage. Suitable Stage 3 media includes Murashige Pre-Transplant Mediums, available from the Carolina Biological Supply Company. The purpose of Stage 3 is to grow individual plantlets and prepare them for greenhouse culture. As distinguished from the prior art process, during Stage 3, the same size or a larger size integument pack 50 can be used. Initially in Stage 3, the plants are still grown in the culture room during this phase of development, but they are placed under increased light conditions so as to promote photosynthesis and growth. Approximately 2000 foot-candles of light are provided. The differentiation and growth process of Stage 3 requires between 20 and 45 days depending upon the plant variety. Because the integument packs 50 are contaminant impermeable, once individual plantlets have formed, the plantlets can be removed to the greenhouse to harden during the later portions of Stage 3 and need not be housed in a culture room for the entire Stage 3 period. This can significantly reduce the time normally required for the hardening process and reduce the size of the culture room.

Some commercial growers will purchase their plants upon completion of Stage 3. Many, however, will wait until the plants have completed Stage 4, the final production stage. If purchased at the end of Stage 3, the plants produced by the inventive process need not be immediately planted. They may be maintained for up to one month simply by keeping the plantlets in their integument packs under conditions of reasonable temperature and light. This is advantageous in commercial production where the Stage 3 plants are sometime shipped directly to the grower, who may lack the time to plant them immediately. In the prior art, since the plantlets have been removed from the sterile environment of the culture room, the commercial grower must immediately remove the plantlets from the shipping containers, rinse them to remove the media in which the contaminants can thrive, and then plant the plantlets immediately. Because the plantlets purchased by growers at the end of Stage 3 are shipped and maintained in the integument packs 50, they are contaminant impermeable and, therefore, without the danger of contamination. The advantage in the new process is that the grower does not have to plant immediately. When the grower is ready to plant, he can simply slit the Stage 3 integument open, rinse and deposit the plantlet into the soil medium.

Stage 4: Greenhouse Culture and Hardening

At Stage 4, the plantlets are removed from the integument packs 50 of Stage 3 and are transferred to a greenhouse where they are individually planted in a soil medium. The plant's tolerance to light must be increased so that the plant can adapt to its natural environment. This process is called "hardening" the plant. The plant's tolerance to light is gradually increased in Stages 3 and 4. During Stage 4, the plants are exposed to up to 8,000 foot-candles in the greenhouse where growth and hardening is to take place. The exposure of the foliage of the plant directly to the atmosphere permits the plantlet to later grow in its natural environment without the protection of the integuments used in Stages 1 to 3.

Figure 8:
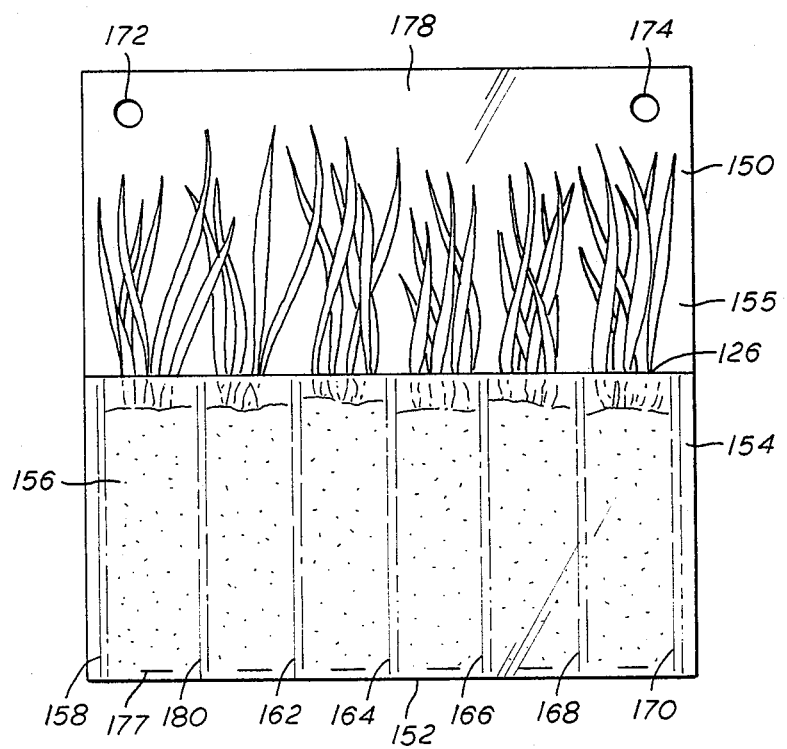
FIG. 8 depicts an array of Stage 4 envelopes, each containing a soil medium for growing Stage 4 plantlets.
Figure 9:
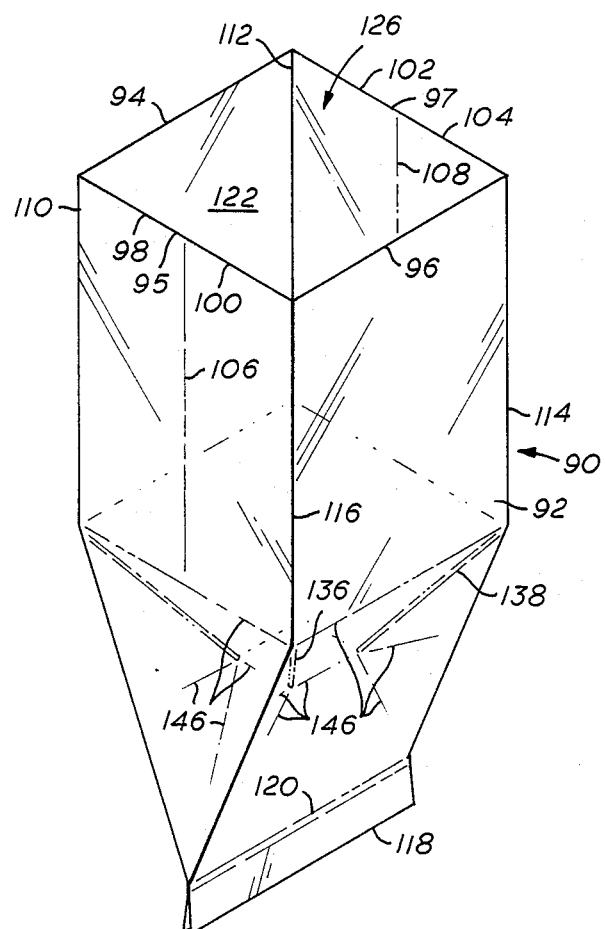
FIG. 9 depicts a perspective view of an alternative embodiment of the integument of FIGS. 1 and 7.
Figure 12:
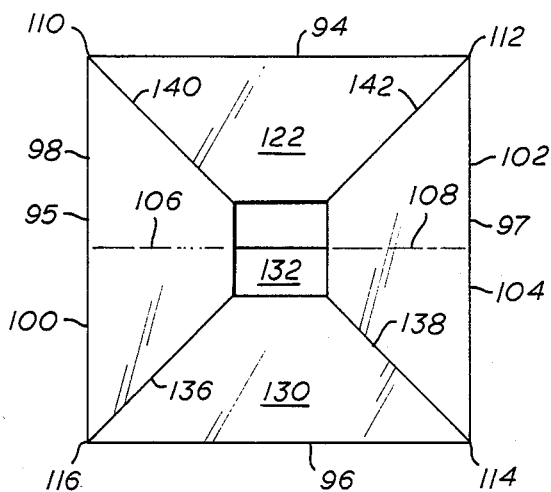
FIG. 12 depicts a top view of the integument of FIG. 10.

Referring now to FIG. 8, there is shown an envelope 150 made of a polyethylene material which can be made of a low density polyethylene which is less expensive than the high density polyethylene that is used for membranes 12 and 92. The envelope 150 has a typical size, depending upon the plant variety, of approximately 12 inches wide and 8 inches high. The material for envelope 150 is translucent to permit the passage and diffusion of light therethrough. To form envelope 150, the material is folded over at 152 forming a base material 155 and a frontal material 154 such that the length of the flap or frontal material 154 folded over is approximately one-half the height of the base material 155 and envelope 150. Individual pockets 156 are created by heat sealing the frontal material 154 longitudinally to the base material 155 at 158, 160, 162, 164, 166, 168 and 170. These heat seals form six individual pockets 156 for housing individual plantlets during Stage 4. The free end of frontal material 154 forms apertures 176 for the insertion of appropriate soil medium and individual plantlets. Slits 177 are provided adjacent the fold at 152 in the bottom of each pocket 156 to permit drainage. The envelope 150 includes connection means 172, 174 adjacent the top thereof for the purpose of vertically suspending envelope 150 by suitable attachment means such as hooks.

Alternatively, the base material 155 and frontal material 154 may be two separate and individual sheets of material as distinguished from the embodiment described above. Further, the width of the frontal material 154, as a separate piece, may be greater than the width of the base material 155 so as to form a bellowing of the frontal material 154 upon heat sealing materials 154, 155 at 158, 160, 162, 164, 166, 168 and 170 and along the entire width thereof at the bottom of pockets 156. The greater width of the frontal material 154 provides excess material at the pockets 156 so as to provide larger pockets 156 than in the embodiment shown in FIG. 8. These enlarged pockets 156 may be desirable for certain sizes and varieties of plants. The width of such an envelope 150 preferably remains the same as the embodiment shown in FIG. 8 since the width of base material 155 does not change. It can be appreciated that the pockets 156 may be dimensioned so as to provide any volume required by a particular variety of plantlets.

Referring again to FIGS. 15 and 16, envelopes 150 may be suspended vertically within the greenhouse using standards 180 and racks 190. Only one envelope 150 is normally supported at a single location as distinguished from integument packs 50 which may be suspended several to a location. However, as shown in FIG. 8, the base material 155 of envelopes 150 provide an upper band 178 extending above the frontal material 154. Adjacent envelopes 150 suspended on rack 190 can be overlapped vertically by the extent of the upper band 178 of base material 155 to save space. The overlapping does not prevent the plantlets in pockets 156 from still being exposed to any overhead misters. It is advantageous to suspend envelopes 150 for many of the same reasons as suspending integument packs 50. In particular, light transmission and air availability for the plantlets in Stage 4 is enhanced by suspending the plantlets in envelopes 150 on either standards 180 or racks 190. During Stage 4 of the prior art process, the plantlets are planted individually in a soil medium contained in small plastic liners which are placed in a flat. These prior art flats are then stored in the greenhouse, often on wooden supports such as tables or benches on the greenhouse floor. Thus, in the prior art, the plantlets are generally placed side by side at a common elevation within the greenhouse to form a mat of plants extending across the greenhouse. By placing the plantlets together as described in the prior art, the plantlets tend to reduce the light that is available to adjacent plants and also cause dead air spaces adjacent the plants, thus inhibiting their growth. Further, the liners, flats or pots are opaque and therefore do not transmit any available light therethrough.

The combination of translucent envelopes 150 and the vertical suspension of envelopes 150 on wire mesh that minimizes light blockage offers greater light transmission and air movement to the plantlets than that of the prior art growing areas which house the plantlets all together at substantially a common elevation. In the present invention, the air flows through the mesh and in between adjacent standards 180 and racks 190. Further, light can pass through the translucent envelopes 150 to reach other envelopes suspended on standards 180 and racks 190 where such light would otherwise be blocked. Where the plantlets were limited to a single level within prior art growing areas, the present invention now allows a plurality of levels of plantlets within the growing area. This markedly reduces the amount of space required for the greenhouse.

The soil used in Stage 4 is typically a pre-sterilized peat moss mix. Depending upon the type of plant, most commercial plants remain in the greenhouse 30 to 90 days before they are shipped to the grower within envelopes 150. The envelopes 150 are advantageous as compared to the prior art plastic liners in a flat, because the envelopes may be rolled up with the plantlets therein so as to consume less space for shipping than the prior art containers. Further, the cost associated with the culture room, greenhouse, and shipping are reduced using the new envelopes 150.

Use of the inventive process permits all stages of the micropropagation process to be less time consuming than their prior art counterparts, because the new and improved integuments are more easily and quickly handled. Thus, more tissue culture samples can be processed per day. Further, because the integuments consume less space than prior art containers, the costs associated with the culture room and the greenhouse are reduced.

TABLES 1 AND 2 the contamination rate using the inventive

Table 1 compares integuments and related process versus the prior art process and containers, in this instance test tubes, using different plants in an environment without sterile filtered air. The tissue samples were cultured for 28 days in each stage under identical conditions, except that 10 ml of media was used with the prior art containers, and 5 ml was used with each of the cellules 72 of the integument packs 50.

TABLE 1

| CONTAMINATIONS PER 200 CULTURES PER STAGE | | | | | | |
|---|---|---|---|---|---|---|
| | STAGE 1 | | STAGE 2 | | STAGE 3 | |
| | Test Tube | Present Invention | Test Tube | Present Invention | Test Tube | Present Invention |
| Alocasia Lindanii (Alocasia) | 66 | 25 | 55 | 0 | 51 | 0 |
| California (Boston Fern) | 61 | 29 | 59 | 0 | 52 | 0 |
| Hillii (Boston Fern) | 73 | 25 | 47 | 0 | 43 | 0 |
| Nephrolepis Biserrata Furcens Fishtail Fern) | 68 | 28 | * | * | * | * |
| Boston Curly Frond (Boston Fern) | * | * | 52 | 12 | * | * |
| Boston Roosevelt Compacta (Boston | * | * | * | * | 44 | 0 |

TABLE 1-continued

CONTAMINATIONS PER 200 CULTURES PER STAGE

| | STAGE 1 | | STAGE 2 | | STAGE 3 | |
|---|---|---|---|---|---|---|
| | Test Tube | Present Invention | Test Tube | Present Invention | Test Tube | Present Invention |
| Fern) | | | | | | |

*These Tables reflect the results of the limited tests which had been conducted at the time of this application. These tests were not conducted pursuant to a predetermined procedure whereby each plant underwent every stage of the micropropagation process. These tests were conducted using available tissue samples from a variety of plants, the tissue samples being in various stages of development. For this reason, certain stages of the micopropagation process were never conducted for cert ain plants.

TABLE 2

TISSUE GROWTH RATES (AVERAGE WEIGHT PER SAMPLE)

| | STAGE 1 (Note 1) | | STAGE 2 (Note 2) | | STAGE 3 (Note 1) | |
|---|---|---|---|---|---|---|
| | Test Tube | Present Invention | Test Tube | Present Invention | Test Tube | Present Invention |
| Alocasia Lindanii (Alocasia) | 0.38 g | 1.70 g | 1.03 g | 4.5 g | 1.52 g | 5.41 g |
| California (Boston Fern) | * | * | 1.03 g | 4.57 g | 1.31 g | 5.47 g |
| Hillii (Boston Fern) | * | * | 0.38 g | 4.38 g | 1.03 g | 5.05 g |
| Boston Curly Frond (Boston Fern) | * | * | 0.39 g | 4.08 g | * | * |
| Boston Roosevelt Compacta (Boston Fern) | * | * | * | * | 1.39 g | 468 g |

*These Tables reflect the results of the limited tests which had been conducted at the time of this application. These tests were not conducted pursuant to a predetermined procedure whereby each plant underwent every stage of the micropropagation process. These tests were conducted using available tissue samples from a variety of plants, the tissue samples being in various stages of development. For this reason, certain stages of the micopropagation process were never conducted for cert ain plants.

Notes:
(1) Plants were grown for 28 days in Stages 1 and 3 using Murashige Minimal Organic in all cases.
(2) Plants were grown for 28 days in Stage 2 using Murashige Fern Multiplication in all cases except for the Alocasia Lindanii, where Murashige Shoot Multiplication A was used.

Tables 1 and 2 illustrate a reduction in contamination and an increase in growth rate and in the number of new tissue cultures and plantlets produced from an individual meristematic tissue of a cultivar using the inventive integuments and related process. For example, the *Alocasia Lindanii* of Table 1 shows that the prior art container and process has 172 contaminated tissue cultures per 600 cultures while the integument and process of the present invention has only 25 contaminated cultures. Thus, the present invention reduced contaminated cultures by approximately 85%. Table 2 shows that the growth of the *Alocasia Lindanii* culture using the integument and process of the present invention had an increase in average weight of approximately 4.5 times over the prior art process during Stage 1, an increase of approximately 4.4 times over the prior art process during Stage 2, and an increase of approximately 3.6 times over the prior art process during Stage 3. Over the three stages, the inventive integument and process produced a growth rate approximately 4 times greater than that of the prior art containers and process.

The following are further examples of the new and improved integument and process in micropropagation.

EXAMPLE I

Tissue Culture of Nephrolepis Exaltata Whitmanii

An experiment was conducted for the micropropagation of the fern *Nephrolepis Exaltata* Whitmanii, wherein the results of employing the integument and process of the present invention were compared with those obtained using the prior art containers and process. Stages 1 to 4 where utilizing the inventive integument and process are described first, followed by a description of the prior art containers and process.

Inventive Integument and Process

In preparing the media for Stage 1 4.4 grams of premixed Murashige Minimal Organic medium and 30 grams of sucrose were added to 500 ml of distilled water. The solution was stirred until the ingredients had dissolved. Additional distilled water was then added to bring the final volume of the solution to 1000 ml. The pH of the solution was then adjusted to 5.5. 8 grams of agar were then added and the mixture was heated until the agar dissolved. 5 ml of the media was then transferred to each of 200 cellules 72 of the integument packs 50. The unsealed ports of entry of the cellules were then covered with nonabsorbent paper towelling and the integument packs were autoclaved for fifteen minutes at 15 psi. The integuments were removed from the autoclave while still warm and placed under a laminar flow hood to complete cooling.

In preparing the meristematic tissue, 250 stolons of the fern were removed from the preselected parent plant and were wrapped in a sterile gauze. This gauze packet containing the stolons was then soaked with 500 ml of sterile distilled water to which two drops of wetting agent, such as Palmolive Green manufactured by Procter & Gamble of Cinncinati, Ohio, had been added. This packet was sonicated for three minutes. The packet was then placed in a sterile container and covered with 500 ml of a 10% sodium hypochloride solution to which two drops of a wetting agent had been added. The container was covered with a tight fitting lid and vigorously shaken by hand for one minute. The container was then placed in the ultrasonic cleaner and sonicated for ten minutes, after which it was then removed and sprayed with a 90% isopropyl alcohol solution and placed in the laminar flow hood to air dry. The lid was removed and the 10% sodium hypochloride solution was drained off.

The gauze packet containing the stolons was then rinsed three times with sterile distilled water (approximately three minutes for each rinse). The packet was removed from the container, laid on a st(R)rile work surface under the laminar flow hood, and the gauze packet was opened. The clean stolons were separated and approximately one inch of the active growing end was removed from each stolon. One active end was placed in each of the cellules 72 containing media.

The top of each cellule was heat sealed using a wire sealer at 300° F. for ten seconds. The integument pack was then labeled and the process was repeated until all the tissue had been so placed.

The integument packs were placed in the culture room, which was maintained at 80° F. with sixteen hours of light and eight hours of darkness per twenty-four hour period. The cultures were examined every twenty-four hours for contamination and growth.

During the first five days of Stage 1, twenty-six of the 200 cultures contaminated. At the end of ten days, some initial growth was observed in all of the remaining cultures. Some frond development was noted in all cultures by the end of the twentieth day, and the cultures were ready for Stage 2 multiplication by the end of the twenty-eighth day.

To prepare the media for Stage 2, 4.6 grams of premixed Murashige Fern Multiplication Medium and 30 grams of sucrose were added to 500 ml of distilled water. This was stirred until a solution was formed. Additional distilled water was added to bring the volume to 1000 ml. The pH was adjusted to 5.3. 8 grams of agar was then added to the solution and the solution was heated until the agar had dissolved. 5 mml of the solution was then added to each of 200 unused cellules 72 of integument packs 50. The open ports of entry of the cellules were covered with nonabsorbant paper towels and the integument packs were autoclaved for fifteen minutes at 15 psi. While still warm, the integument packs were moved to the laminar flow hood and allowed to cool.

To prepare the tissue cultures from Stage 1, the integument packs containing active clean cultures from Stage 1 were first completely immersed in a 10% sodium hypochloride solution for three minutes, then removed and rinsed with sterile water. The integument packs were dried with a sterile paper towel and laid on a sterile work surface under the laminar flow hood.

One cellule was opened at a time, using a sterilized No. 11 scalpel, by making a lengthwise cut down the center of the cellule. The tissue samples were removed with sterilized instruments and placed on a sterile work surface. If more than one active growing point was present on the removed tissue sample, the sample was divided into individual growing points. These individual growing points were then planted in the prepared cellule containing the Stage 2 multiplication media. After the cellules were filled, they were sealed using the above-described wire heat sealer.

The Stage 2 integument packs were then labeled and moved to the culture room, which was maintained at 80° F. with sixteen hours of light and eight hours of darkness per twenty-four hours. The cultures were checked every 24 hours for contamination and growth.

During the 28 day test period no contamination was noted in any of the cultures. During the first ten days, accelerated growth was noted in all cultures. At the end of twenty-eight days, the cultures were ready for stage 3.

In preparing the media for Stage 3, 4.4 grams of premixed pretransplant medium was mixed with 30 grams of sucrose and added to 500 ml of distilled water. This was then stirred until the ingredients had dissolved. Additional distilled water was added to bring the volume to 1000 ml. The pH was then adjusted to 5.5. 8 grams of agar was added, and the solution was heated until the agar had dissolved. 5 ml of the media was placed in each unused Stage 3 cellule 72 of integument pack 50. The unsealed ports of entry of the Stage 3 cellules were then covered with non-absorbant paper towelling and the integument packs were autoclaved for fifteen minutes at 15 psi. While still warm, the integument packs were removed from the autoclave and placed in the laminar flow hood to finish cooling.

The tissue samples emerging from the Stage 2 cellules were used as the Stage 3 source materials. The Stage 2 integument packs were first immersed in 10% sodium hypochloride solution for three minutes, and then rinsed in distilled water. The integument packs were dried with sterile paper towelling and placed on a sterile work surface under the laminar flow hood. Each cellule of the integument pack was opened by cutting lengthwise down its center with a sterile scalpel. The tissue was removed, placed on a sterile work surface, and then rinsed with sterile water and blotted dry with sterile paper towelling. Each tissue sample was then weighed. The average weight per sample was 4.5 grams.

The tissue emerging from Stage 2 was then subdivided into as many pieces of active growing tissue as could feasibly support good Stage 3 growth. Each division was then placed in a cellule 72 of an unused integument pack 50 which was sealed using the wire sealer at 300° F. for ten seconds.

The integument packs were then labeled and moved to the culture room maintained at 80° F. with sixteen hours of light and eight hours of darkness per each twenty-four hours. The cultures were checked every twenty-four hours for contamination and growth.

During the twenty-eight day test of Stage 3, no contamination was observed in any culture. Root development was noted at the end of the first week and good frond development appeared by the end of the second week.

After twenty-eight days, the resulting plantlets were ready to enter Stage 4. Under the laminar flow hood, the plantlets were removed from the integument packs, rinsed with distilled water, blotted dry and weighed. The average weight was 5.4 grams per tissue sample.

The Prior Art Process

The media preparation for the prior art process was the same as described above, except that twice as much media was prepared, and, rather than being placed into the integuments of the present invention, 10 ml of media was placed into each of 200 25×150 mm sterlized test tubes. The tubes were capped with conventional plastic caps.

The tissue preparation for the *Nephrolepis Exaltata Whitmanii* was also the same as described above. However, the results obtained following Stage 1 were dramatically different. Twenty cultures became contaminated during the first 5 days, and an additional 26 were lost during the 28 day Stage 1 period. It was not until the 15th day that all tissue samples showed some growth, and by the 20th day only one half of the samples showed frond development.

The Stage 2 media was the same as that described above, except that, once again, twice as much was prepared and placed into each Stage 2 test tube. The Stage 1 test tubes could not be immersed in the sodium hypochloride solution because there would be leakage through the caps. Instead, under the laminar flow hood, their outer surfaces were sterilized by spraying with a 90% isopropyl alcohol solution before the tissue samples were removed from their Stage 1 test tubes and placed into Stage 2 containers.

During the first 5 days of Stage 2 growth, 18 cultures became contaminated, and an additional 38 samples were lost to contamination between the 14th and 28th days. It was not until the 10th day that accelerated growth in the samples was observed. The average weight per sample at the completion of the 28 day Stage 2 was only 1.03 grams as compared to 4.5 grams using the inventive integument and process.

For Stage 3, once again twice as much media as that used with the inventive process was prepared and placed into each Stage 3 test tube. Again, rather than immersing the Stage 2 test tubes in sodium hypochloride solution, the outer surface was sprayed with the alcohol solution while under the laminar flow hood.

During the first 5 days of Stage 3 growth, 18 cultures became contaminated, and an additional 35 samples were lost to contamination between the 14th and 28th days. Root development did not appear on the majority of samples until the 14th day, and minimal frond development did not appear until the 24th day. The average weight per sample at the completion of the 28 day Stage 3 was only 1.3 grams as compared to 5.4 grams using the inventive integument and process. At this point, the majority of the samples were not ready for transfer to Stage 4. It is estimated that such samples would have required approximately 45 days of Stage 3 growth to achieve the size and maturity necessary for transfer to Stage 4.

EXAMPLE II

Lettuce Production From Tissue Culturing

Lettuce was produced in tissue culture using the inventive integument and process, as described below.

The Stage 1 media preparation was the same as that described above for the *Nephrolepis Exaltata Whitmanii*.

A non-heading lettuce variety known as butter leaf was selected. This variety has a normal production time from seed of 45 to 50 days. Tissue was first removed from the apical dome of thirty greenhouse-raised plants. The leaves were stripped, and the roots were removed exposing the stem, which was rinsed in running water. The apical dome was then removed.

The apical dome was placed in a clean container and covered with 10% sodium hypochloride solution to which two drops of a wetting agent had been added. This was sonicated for ten minutes and the tissue was rinsed three times in sterile distilled water.

Under the laminar flow hood, final tissue samples, which were still covered with leaf, were excised from the primary apical dome of the plant and subdivided three to four times to yield 100 tissue samples. Each individual tissue sample was placed in the cellule 72 of an integument pack 50, already each containing 5 ml of Stage 1 media. Each cellule was then sealed using a wire sealer at 300° F. for ten seconds. The integument packs were labelled and moved to the culture room which was maintained at the same temperature and light conditions as described with respect to Example I. The cultures were examined every twenty-four hours for growth and contamination.

During the first five days, thirty-five cultures contaminated, but no further contamination occurred. On the fifth day, good root development was noted in all the remaining cultures, and by the end of the seventh day, all cultures had developed leaves and were actively growing. A tremendous increase in tissue mass was noted by the end of the tenth day, at which time a majority of the cultures had developed one inch long leaves. By the twenty-eighth day, the average leaf size was three inches, and all cultures were ready for Stage 2.

In preparing the media for Stage 2, 4.8 grams of Murashige Premixed Multiplication Medium A and 30 grams of sucrose were added to 500 ml of water. This was stirred until the ingredients had dissolved and distilled water was added to make the final volume 1000 ml. The pH was adjusted to 5.5. 8 grams of agar was then added to the solution, and it was heated until the agar had dissolved. 5 ml of media was put into each cellule 72 of integument packs 50. The open ports of entry of the cellules were covered with nonabsorbent paper towelling and the integument packs were autoclaved for fifteen minutes at 15 psi. While still warm, the integument packs were placed in the laminar flow hood to complete cooling.

The tissue samples emerging from Stage 1 were used for Stage 2 cultures.

The Stage 1 integument packs were completely immersed in a 10% sodium hypochloride solution for three minutes to effect surface sterilization. They were then rinsed in sterile water and dried with sterile paper towelling. Under the laminar flow hood, the cellules were individually opened by cutting lengthwise down the center, and the tissue was removed and placed in a sterile work surface under the laminar flow hood. All roots and leaves were removed from the tissue and, where possible, the remaining tissue was subdivided. The subdivided tissue samples were then placed into the unused Stage 2 integument packs, one tissue sample per cellule. After each cellule was filled, it was heat sealed with the wire sealer.

All integument packs were labelled and placed in the culture room, maintained at the light and temperature conditions as described with respect to Example I. The cultures were examined every twenty-four hours for growth and contamination.

No Stage 2 cultures were lost to contamination. By the end of the fifth day, there was a substantial increase in the tissue mass. By the tenth day, there was good root development along with primary leaf development. By the end of the fifteenth day, clearly defined plantlets were visible in locations which indicated that lateral buds had developed. The lateral buds continued to grow until the end of the twenty-eight day test period. By this time, well-developed plantlets were ready for additional subculture.

To prepare the media for Stage 3, 4.4 grams of premixed transplant medium and 30 grams of sucrose were added to 500 ml of distilled water. The solution was stirred until the ingredients were dissolved. Additional distilled water was added to make the final volume 1000 ml. The pH was adjusted to 5.5.

50 ml of this media was dispensed into the alternative integument embodiment 90 specially designed to promote the growth of leafy vegetables. The integument employed was twelve inches long with a three inch long root chamber at the base.

The open ports of entry of the cellules 122 of integument 90 were folded over and closed with paper clips and the integuments 90 were then autoclaved for fifteen minutes at 15 psi. While still warm, the integuments were moved to the laminar flow hood to finish cooling.

The active tissue samples from Stage 2 were used as source materials. The Stage 2 integuments were immersed in a 10% sodium hypochloride solution for three minutes to effect surface sterilization, then rinsed in sterile water, dried with sterile paper towels, and laid on a sterile work surface under the laminar flow hood. The cellules 122 of the integuments 90 were opened by cutting lengthwise down their centers, after which the tissue was removed and placed on the sterile work surface.

Individual plantlets were then removed from the primary tissue mass, and were placed in the center of each of the integuments 90 specially designed for leafy vegetable growth. The top of each integument 90 was then sealed with the wire sealer at 300° F. for twenty seconds. The integuments were labeled and moved to the culture room which was maintained at the light and temperature conditions as described with respect to Example I.

No contamination was noted in any of the cultures. By the end of the fifth day, all cultures showed good root development. Leaf development was noted on the sixth day, and it progressed very rapidly. Leaves three inches long were observed in all cultures by the fifteenth day, and full leaf development was noted on the thirtieth day. Complete lettuce plants were harvested on the thirty-fifth day. All had well-developed leaves suitable for consumption. The plants averaged seven inches in length, this measurement being taken from the bottom of the lowest leaf to the top of the plant. The plants also had well-developed interiors with densely packed leaves. Normally, this type of lettuce is non-heading and it takes 45-50 days to produce a similar sized plant from seed.

EXAMPLE III

Lettuce Production from Seed

An experiment was conducted to determine whether the use of the integument and method of the present invention enhanced lettuce growth when lettuce was grown from seed. The experiment was conducted as described below.

The media used was Murashige Minimal Organic, with 30 grams of sucrose and 8 grams of agar dissolved therein by the techniques described above for *Nephrolepis Exaltata Whitmanii*. The final pH was adjusted to 5.5. 5 ml of the media was then placed into the cellules 72 of integument packs 50 depicted in FIG. 7.

Black-seeded Simpson lettuce was used. Two hundred commercially obtained seeds were wrapped in gauze and surface sterilized by sonicating for ten minutes in a 10% sodium hypochloride solution to which two drops of a wetting agent had been added. The gauze packet was then removed and rinsed three times in sterile distilled water, with each rinse lasting for three minutes. The gauze packet was then placed on a sterile work surface under a laminar flow hood and the seeds were separated into two equal groups of 100 each. One hundred of the seeds were planted in the cellules 72 of integument packs 50 with one seed per cellule 72.

After each cellule 72 was filled, it was sealed, labeled and placed in the culture room where it was checked daily for growth and contamination.

The other 100 seeds were planted in a seed starting mix consisting of peat moss, pearlite and vermiculite. The seed was sown on the top of the pre-moistened mix, and pressed into the soil. The flat was labeled and placed in the culture room under the same light and temperature conditions as the seeds planted in the integuments, the same conditions described in Example I.

In the first five days, three cultures in the integuments were lost to contamination. Root development was noted in all cellules by the end of the third day, and primary leaf development was noted on the fourth day. Well-developed seedlings were observed in the integuments on the fifth day.

By the end of the seventh day, no growth was noted in the planted seeds, and a problem was suspected. A microscopic observation revealed evidence of fungal attack on all the seeds. It is suspected that the surface sterilization of the seed removed some natural fungal defense mechanism. The experiment was terminated at this point and repeated as described below.

200 seeds of the black seeded Simpson were obtained as described above. This time, however, only the 100 seeds which were intended for planting in the integuments were treated with the sodium hypochloride solution and sonicated as described above. These 100 seeds were planted in cellules 72 of integument packs 50 containing the same media described above.

The other 100 untreated seeds were pressed into the freshly prepared pre-moistened soil mix described above. Both the integument packs 50 and the flats with the untreated seeds were then placed into the culture room, which was maintained an 80° F. with 16 hours of light and 8 hours of darkness per day. Both the integument packs and flats were checked daily for contamination and germination. The soil in the flats was misted daily to moisten the soil.

During the first five days, two cultures in the integument packs were lost to contamination. Root development was noted in the third day with primary leaf development occurring on the fourth day. Well-developed seedlings were observed on the fifth day. By the end of the tenth day, the seedlings in the integument packs had grown to over one inch in length and had well-developed root systems. At the end of the twenty day test period, these seedlings had filled the cellules of the integument packs with well-developed leaves. 98% of the seeds in the integument packs germinated.

Only 30% of the seeds planted in the soil mix first showed primary leaf development on the seventh day. By the end of the eighth day, only 68 of the 100 seeds had germinated. Root development was not observable as the roots were beneath the soil. The final resultant seedlings averaged only one inch in height with one to two secondary leaves. Eight additional seedlings were lost. At the end of the test, only 60% of the starting seeds originally planted in soil had produced seedlings.

While this experiment was conducted through the use of integument packs 50 such as illustrated in FIG. 7, given the high germination rates of the seeds grown using the inventive process, it is preferable to grow lettuce from seed in an integument 90 such that the plantlets produced would not have to be transferred from an integument pack 50 to an integument 90. Due to the low cost of the integument 90 and the seed itself, any integument 90 containing a seed which fails to germinate can easily be identified and disposed of. Further, eliminating the steps of transferring plantlets from integument packs 50 to integuments 90 would eliminate the significant labor costs otherwise incurred.

Examples I, II and III above demonstrate that the integument and method of the present invention yields dramatic improvements in plant micropropagation and tissue culturing. These same improvements will follow irrespective of whether the plants cultured are horticultural, agricultural or even aquatic in variety. Further, it is believed that the invention will yield dramatic improvements in animal and human tissue culturing.

The Examples and embodiments described are exemplary only and not limiting. Many variations and modifications of the processes and the integuments are possible, and are within the scope of the invention. Accordingly, the scope of protection is not limited by the above description but only by the claims which follow, and that scope includes all equivalents of the subject matter of the claims.

I claim:

1. A tissue culturing system for an atmospheric ambient environment, comprising:
   plant tissue;
   a tissue culturing medium for said plant tissue;
   a gas permeable, liquid impermeable, and translucent membrane having interstices smaller than a virus forming a cellule for enclosing the plant tissue and tissue culturing medium, the gas mixture and pressure within said cellule and the gas mixture and pressure of the atmospheric ambient environment being permitted to equalize by gas exchange through said membrane; said membrane being completely sealed around the plant tissue and tissue culturing medium for preventing the exposure of the plant tissue and tissue culturing medium to biological contaminants in the atmospheric ambient environment.

2. The integument of claim 1 wherein said membrane is made of high density polyethylene.

3. An integument for the micropropagation of plant tissue in the ambient environment, comprising:
   a gas permeable and liquid impermeable membrane forming a cellule for enclosing the tissue, said membrane being completely sealed around the tissue for preventing the exposure of the tissue to biological contaminants in the ambient environment, and said membrane being made of Chevron high density polyethylene 9650 which will prevent oxygen and carbon dioxide to diffuse therethrough.

4. A system for plant production, comprising:
   a plant;
   a medium for said plant;
   a gas permeable, liquid impermeable, translucent membrane made of lightly cross-linked layers of polymers and having a moisture vapor transmission rate equal to that of a high density polyethylene film with a thickness in the range of 1 to 1.5 mils, said membrane having interstices smaller than the size of a virus but large enough for gas exchange, said membrane forming a cellule for enclosing said plant and medium, said cellule being completely sealed around the plant for preventing the exposure of the plant to biological contaminants in the ambient environment.

5. An integument for the micropropagation of plant tissue in the ambient environment, comprising:
   a gas permeable and liquid impermeable membrane forming a cellule for enclosing the tissue, the gas mixture and pressure within the cellule being substantially the same as the gas mixture and pressure of the ambient environment upon enclosure; said membrane being completely sealed around the tissue for preventing the exposure of the tissue to biological contaminants in the ambient environment, said membrane having a molecular structure with interstices smaller than the size of a virus but large enough for gas exchange.

6. An integument for the micropropagation of plant tissue in the ambient environment, comprising:
   a gas permeable and liquid impermeable membrane forming a cellule for enclosing the tissue, the gas mixture and pressure within the cellule being substantially the same as the gas mixture and pressure of the ambient environment upon enclosure; said membrane being completely sealed around the tissue for preventing the exposure of the tissue to biological contaminants in the ambient environment, said membrane having interstices no greater than 0.01 micrometers in size but large enough for gas exchange.

7. An integument for containing a growing plant in a medium in an atmospheric ambient environment, comprising:
   a gas permeable and liquid impermeable membrane of Chevron high density polyethylene 9650 forming a cellule for enclosing the plant, said membrane being completely sealed around the plant for preventing the exposure of the plant to contaminants in the atmospheric ambient environment, said membrane being translucent to permit light to impinge on the plant.

8. An integument free of an internal soil containment device for the growing of plants in the atmospheric ambient environment consisting of:
   a medium for growing the plants; and
   a translucent, gas permeable and liquid impermeable membrane of high density polyethylene forming a cellule for enclosing the plant and medium, said membrane having interstices smaller than the size of a virus and being completely sealed around the plant and medium for preventing exposure of the plant to contaminants in the atmospheric ambient environment; said membrane transmitting therethrough light rays having a wavelength between 400 and 750 nanometers.

9. An integument for the micropropagation of plant tissue in a tissue culturing medium, comprising:
   a membrane forming at least one cellule for containing and completely enclosing the plant tissue and tissue culturing medium;
   said membrane being made of a single layer of high density polyethylene and having interstices smaller than a virus;
   said membrane being semipermeable and allowing the diffusion of gases therethrough; and
   said integument being liquid impermeable and translucent allowing the transmission of light therethrough except for any light blocked by the plant tissue and tissue culturing medium.

10. An integument for growing a plant in a medium in the atmospheric ambient environment comprising:
    a membrane forming at least one cellule for containing and completely enclosing the plant and medium;
    said membrane being made of a single layer of high density polyethylene and having interstices smaller than the size of a virus;
    said membrane being gas permeable for allowing the diffusion of gases therethrough;
    said membrane being liquid impermeable and translucent allowing the transmission of light therethrough;
    said membrane sealing the plant from biological contaminants in the atmospheric ambient environment.

11. A plant production system, comprising:
    a plant;
    medium for growing said plant;

a membrane forming at least one cellule for containing and completely enclosing the plant and medium;

said membrane being made of Chevron 9650 high density polyethylene;

said membrane being semipermeable and allowing the diffusion of gases therethrough; and said membrane being liquid impermeable.

12. An integument for the micropropagation of plant tissue in a tissue culturing medium, comprising:

a membrane forming at least one cellule for containing and completely enclosing the plant tissue and tissue culturing medium;

said membrane being made of a single layer of high density polyethylene;

said membrane being semipermeable and allowing the diffusion of gases therethrough;

said integument being translucent and allowing the transmission of light therethrough except for any light blocked by the plant tissue and tissue culturing medium; and said membrane having a permeability to water vapor of substantially 0.32 grams per 100 square inches per 24 hours.

13. The integument of claim 10 wherein said membrane will withstand autoclaving without melting or distending.

14. An integument for the micropropagation of plant tissue in a tissue culturing medium, comprising:

a membrane forming at least one cellule for containing and completely enclosing the plant tissue and tissue culturing medium;

said membrane being made of a single layer of high density polyethylene;

said membrane being semipermeable and allowing the diffusion of gases therethrough;

said integument being translucent and allowing the transmission of light through the integument except for any light blocked by the plant tissue and tissue culturing medium; and said membrane being made of Chevron high density polyethylene 9650.

15. An integument for growing plant tissue in a tissue culturing medium, comprising:

a high density polyethylene material forming at least one chamber;

said high density polyethylene material being translucent, permeable to gases and impermeable to liquids;

said high density polyethylene having interstices smaller than the size of a virus but large enough for gas exchange;

said high density polyethylene material having the characteristic of withstanding the required temperatures and pressures of an autoclave for sterilization;

said integument allowing light to pass completely therethrough; and said chamber having an aperture for receiving the plant tissue and tissue culturing medium, said aperture being adapted for closure after said chamber receives the plant tissue and tissue culturing medium.

16. The integument of claim 15 wherein said chamber is formed by attaching at predetermined locations adjacent layers of said polyethylene material.

17. The integument of claim 16 wherein said chamber is formed by one sheet of said polyethylene folded over and heat sealed along its open sides.

18. The integument of claim 16 wherein said adjacent layers of polyethylene are heat sealed to form a plurality of chambers.

19. The integument of claim 18 wherein said chambers are expandable and permit the passage of light therebetween.

20. The integument of claim 15 wherein said material further forms a band above said chamber for suspending said chamber in the vertical position.

21. The integument of claim 20 wherein said band includes attachment means for attaching said flap to a support.

22. An integument for growing plant tissue in a tissue culturing medium, comprising:

a high density polyethylene material forming at least one chamber;

said high density polyethylene material being translucent and permeable to gases and impermeable to liquids;

said high density polyethylene material having the characteristic of withstanding the required temperatures and pressures of an autoclave for sterilization;

said integument allowing light to pass completely therethrough; and said chamber having an aperture for receiving the plant tissue and tissue culturing medium, said aperture being adapted for closure after said chamber receives the plant tissue and tissue culturing medium, and said polyethylene material being substantially 1.25 mils in thickness.

23. An integument for growing plant tissue in a tissue culturing medium, comprising:

a high density polyethylene material forming at least one chamber;

said high density polyethylene material being translucent and permeable to gases and impermeable to liquids;

said high density polyethylene material having the characteristic of withstanding the required temperatures and pressures of an autoclave for sterilization;

said integument allowing light to pass completely therethrough;

said chamber having an aperture for receiving the tissue and tissue culturing medium, said aperture being adapted for closure after said chamber receives the tissue and tissue culturing medium;

said chamber being divided into a foliage chamber and a root chamber, said root chamber accommodating the root system of the plant tissue and containing the tissue culturing medium.

24. The integument of claim 15 further including a support for suspending said chamber in a vertical position.

25. An integument pack for growing plant tissue in a tissue culturing medium, comprising:

adjacent layers of gas permeable, liquid impermeable and translucent material being attached together at predetermined locations thereof to form a plurality of cellules for receiving the plant tissue and tissue culturing medium;

said cellules being adapted for closing upon receiving the plant tissue and tissue culturing medium whereby the plant tissue is completely enclosed from the ambient environment;

said material having light transmission properties which allow light rays having wavelengths in the range of 400 to 750 nanometers to pass through said material; and said material having a molecular structure forming interstices sized to allow the diffusion of oxygen and carbon dioxide therethrough but preventing the passage of viral biological contaminants.

26. An integument for the micropropagation of a leafy vegetable tissue in a medium, comprising:

a gas permeable, liquid impermeable, and translucent membrane having interstices smaller than a virus forming a cellule to receive the leafy vegetable tissue and medium;

said cellule having a foliage chamber and separate root chamber made with said membrane with a reduced opening therebetween whereby the root system grown by the tissue extends from said foliage chamber, through said reduced opening and into said root chamber containing the medium.

27. A system for seed germination, comprising:

a seed;

a medium for germinating said seed;

a gas permeable, liquid impermeable membrane forming a cellule for enclosing said seed and medium, said membrane having interstices smaller than a virus and being completely sealed around the seed for preventing the exposure of the seed to biological contaminants in the atmospheric ambient environment, and said membrane being a semipermeable and translucent membrane.

28. An integument for germinating a seed in a medium, comprising:

a gas permeable, liquid impermeable membrane of Chevron 9650 high density polyethylene forming a cellule for enclosing the seed, said membrane being completely sealed around the seed for sealing the seed from biological contaminants in the ambient atmosphere.

29. The integument of claim 26 wherein said foliage chamber and root chamber are formed by attaching adjacent walls of said cellule at predetermined locations; said attachment locations not completely extending across said cellule so as to form said opening.

30. The integument of claim 29 wherein said attachment locations are at an angle of less than 90 degrees with the central axis of said cellule so as to form a conical shaped end to said foliage chamber.

31. A support for the micropropagation of plant tissue comprising:

a frame;

a plurality of integuments having cellules containing the plant tissue and sealing the plant tissue from biological contaminants in the ambient environment, said integuments having a band above said cellules for attachment to said frame; and said integuments being made of a gas permeable, liquid impermeable material having interstices smaller than a virus, said material being translucent such that light may pass completely through one integument and into an adjacent integument.

32. A method for growing plant tissue in an integument in an atmospheric ambient environment, comprising the steps of;

inserting the plant tissue and a tissue culturing medium in the cellule of the integument; said integument being made of a gas permeable, liquid impermeable and translucent membrane of high density polyethylene;

completely enclosing the plant tissue within the cellule;

sealing the plant tissue from the biological contaminants in the ambient environment;

transmitting light through the translucent membrane to the plant tissue, any light not blocked by the plant tissue and tissue culturing medium passing completely through the integument; and diffusing oxygen and carbon dioxide through said membrane to permit the plant tissue to breathe.

33. A method of micropropagation of plant tissue comprising the steps of:

placing within the cellule of an integument formed of Chevron high density polyethylene #9650 a tissue culturing medium which is suitable for establishing an initial culture of primarily undifferentiated plant tissue;

placing a plant tissue within the cellule and sealing the plant tissue and initial tissue culturing medium from biological contaminants in the ambient environment;

establishing an initial culture of primarily undifferentiated plant tissue;

transferring a portion of the plant tissue established in the initial culture to a second cellule of another unused integument having a tissue culturing medium suitable for multiplication of the plant tissue therein;

multiplying the transferred portion of the plant tissue into a mass of plant tissue of primarily undifferentiated plant tissue;

transferring a portion of multiplied plant tissue to a third cellule of another unused integument having therein a tissue culturing medium suitable for individual plant formation.

34. A method of micropropagation of plant tissue in an atmospheric ambient environment comprising the steps of:

(a) providing a pliable cellule made of a gas permeable, liquid impermeable, translucent membrane having interstices smaller than a virus but large enough for gas exchange;

(b) inserting a tissue culturing medium into the cellule for establishing an initial culture;

(c) sterilizing the cellule containing the tissue culturing medium;

(d) inserting plant tissue into the tissue culturing medium;

(e) enclosing the plant tissue within the cellule and sealing the plant tissue completely within the cellule to protect the plant tissue from biological contaminants in the ambient environment;

(f) exposing all parts of the plant tissue to the light transmitted and the gas exchanged through the membrane;

(g) transmitting light through the entire surface of the cellule to all parts of the plant tissue; and (h) exchanging gas through the surface of the cellule to all parts of the plant tissue.

35. A method of micropropagation of plant tissue in an atmospheric ambient environment comprising the steps of:

(a) providing an unused pliable cellule made of a gas permeable, liquid impermeable, translucent membrane having interstices smaller than the size of a virus but large enough for gas exchange;

(b) inserting a tissue culturing medium for tissue multiplication into the cellule;

(c) sterilizing the cellule containing the tissue culturing medium;

(d) removing the plant tissue from another cellule containing primarily undifferentiated plant tissue;

(e) dividing the plant tissue into individual growing point tissues;

(f) inserting an individual growing point tissue in the cellule of the sterilized unused cellule containing the tissue culturing medium;

(g) enclosing the individual growing point tissue completely within the cellule and sealing the growing point tissue from biological contaminants in the ambient environment;

(h) exposing all parts of the growing point tissue to the light transmitted and gas exchanged through the membrane;

(i) transmitting light through the surface of the cellule to all parts of the growing point tissue; and (j) exchanging gas through the surface of the cellule to all parts of the growing point tissue.

36. A method of micropropagation of plant tissue in an atmospheric ambient environment comprising the steps of:

(a) inserting a tissue culturing medium for individual plant formation into a new pliable cellule which is made of a gas permeable, liquid impermeable, translucent membrane having interstices smaller than a virus but large enough for gas exchange;

(b) sterilizing the cellule containing the tissue culturing medium;

(c) removing plant tissue from another cellule containing primarily undifferentiated plant tissue and disposing of that another cellule;

(d) inserting the plant tissue removed from the plant tissue containing cellule into the sterilized cellule containing the tissue culturing medium;

(e) enclosing the plant tissue within the sterilized cellule and sealing the plant tissue completely within the cellule to protect the tissue from biological contaminants in the ambient environment;

(f) exposing all parts of the plant tissue to the light transmitted and gas exchanged through the cellule;

(g) transmitting light through the surface of the cellule to all parts of the plant tissue; and (h) exchanging gas through the surface of the cellule to all parts of the plant tissue.

37. A method of micropropagation of plant tissue comprising the steps of:

(a) dissolving a minimal organic medium and sucrose with distilled water to form a media solution;

(b) adjusting the pH of the media solution;

(c) transferring the media solution to a pliable cellule made of Chevron high density polyethylene #9650;

(d) autoclaving the cellule and placing the cellule under a laminar flow hood;

(e) removing differentiated tissue from a cultivar;

(f) performing surface sterilization of the plant tissue;

(g) transferring the plant tissue to the cellule under the laminar flow hood;

(h) enclosing the plant tissue within the cellule and sealing the plant tissue completely within the cellule to protect the plant tissue from biological contaminants in the ambient environment;

(i) placing the integument in a culture room;

(j) exposing all parts of the plant tissue to the light transmitted and gas exchanged through the cellule;

(k) transmitting light through the surface of the cellule to all parts of the plant tissue;

(l) exchanging gas through the surface of the cellule to allow the plant tissue to grow into a mass of primarily undifferentiated tissue; and (m) removing the integument from the culture room upon certification that the resultant plant tissue mass is contaminant free.

38. A method of micropropagation of plant tissue comprising the steps of:

(a) dissolving a multiplication medium and sucrose with distilled water forming a media solution;

(b) adjusting the pH of the media solution;

(c) transferring the media solution to a new cellule of Chevron high density polyethylene #9650;

(d) autoclaving the new cellule and placing the cellule under a laminar flow hood;

(e) immersing a cellule containing a mass of primarily undifferentiated and certified contaminant-free plant tissue in a sterilizing agent;

(f) placing the tissue-containing cellule under a laminar flow hood;

(g) opening the tissue-containing cellule and removing the plant tissue mass from the cellule with sterilized instruments and disposing of the used cellule;

(h) dividing the plant tissue mass into individual growing point plant tissues;

(i) inserting an individual growing point plant tissue in the new cellule containing the media solution under the laminar flow hood;

(j) enclosing a growing point plant tissue within the cellule and sealing the plant tissue completely within the cellule to protect the plant tissue from biological contaminants in the ambient environment;

(k) placing the integument in a culture room;

(l) exposing all parts of the growing point plant tissue to the light transmitted and gas exchanged through the cellule;

(m) transmitting light through the surface of the cellule to all parts of the growing point plant tissue;

(n) exchanging gas through the surface of the cellule to allow the growing point plant tissue to grow into a mass of primarily undifferentiated plant tissue; and (o) repeating steps (a) through (n) using the growing point tissue until a predetermined number of plant tissue masses have been produced.

39. A method of micropropagation of plant tissue comprising the steps of:

(a) dissolving a pretransplant medium and sucrose with distilled water forming a media solution;

(b) adjusting the pH of the media solution;

(c) transferring the media solution to a new pliable cellule of Chevron high density polyethylene #9650;

(d) autoclaving the new cellule and placing the cellule under a laminar flow hood;

(e) immersing a cellule containing a sample of primarily undifferentiated growing plant tissue in a sterilizing agent;

(f) placing the tissue-containing integument under a laminar flow hood;

(g) opening the tissue-containing cellule and removing the plant tissue from the cellule with sterilized instruments and disposing of the used cellule;

(h) inserting the plant tissue in the new cellule containing the media solution under the laminar flow hood;

(i) enclosing the plant tissue within the cellule and sealing the plant tissue completely within the cellule to protect the plant tissue from biological contaminants in the ambient environment;

(j) placing the integument in a culture room:

(k) exposing all parts of the plant tissue to the light transmitted and gas exchanged through the cellule;

(l) transmitting light through the surface of the cellule to all parts of the plant tissue;

(m) exchanging the gas through the surface of cellule to all parts of the plant tissue; and (n) removing the plant tissue from the cellule upon the plant tissue growing into a plantlet.

40. A method of producing a plant from a seed in the atmospheric ambient environment, comprising:

(a) dissolving an organic medium and sucrose with distilled water forming a media solution;

(b) adjusting the pH of the media solution;

(c) transferring the media solution to a new pliable cellule of a gas permeable, liquid impermeable, and translucent membrane having interstices smaller than a virus but large enough for gas exchange;

(d) surface sterilizing the seed;

(e) rinsing the seed in distilled water and placing under a laminar flow hood;

(f) transferring the seed to the cellule under the laminar flow hood;

(g) enclosing the seed within the cellule and sealing the seed completely within the cellule to protect the seed from biological contaminants in the ambient environment;

(h) placing the cellule in a culture room;

(i) exposing all parts of the seed to the light transmitted and gas exchanges through the cellule;

(j) removing the plantlets from the cellule upon development of foliage and a root system;

(k) transferring the plantlet to an unused cellule; and (l) removing the plant upon growth.

41. A combination conducive to tissue growth in an atmospheric ambient environment, comprising:
a cell; and
a gas permeable and liquid impermeable membrane of Chevron high density polyethylene #9650 forming a cellule for completely enclosing said cell and creating a closed environment for the cell, said membrane sealing said cell from biological contaminants in the atmospheric ambient environment.

42. The combination of claim 41 where said cell is alive and reproducing.

43. The combination of claim 41 further including a tissue culturing medium disposed within said cellule for supporting the growth of said cell and said membrane being translucent such that the combination includes only said cell, tissue culturing medium and membrane whereby any light not blocked by said cell and said tissue culturing medium is allowed to pass through the combination.

44. A combination conducive to cell growth in a tissue culturing medium in an atmospheric ambient environment, comprising:
a cell;
a tissue culturing medium;
a gas permeable, liquid impermeable, and translucent membrane forming a cellule for completely enclosing said cell and tissue culturing medium; said cellule creating a closed environment for said cell, said membrane having interstices smaller than the size of a virus and sealing said cell from biological contaminants in the ambient environment; and
said membrane permitting oxygen and carbon dioxide to diffuse therethrough.

45. A combination conducive to plant tissue growth in a tissue culturing medium in an atmospheric ambient environment comprising:
plant tissue;
a tissue culturing medium;
a container for receiving and enclosing said plant tissue and tissue culturing medium, said entire container being pliable and completely sealed around said plant tissue and said tissue culturing medium for preventing the exposure of said plant tissue and said tissue culturing medium to biological contaminants in the atmospheric ambient environment, said container being made of a single layer of translucent, liquid impermeable, and gas permeable membrane with a molecular structure having interstices smaller than a virus but large enough for gas exchange.

46. The combination of claim 45 wherein said container is made entirely of said membrane, wherein said membrane is Chevron 9650 high density polyethylene film.

47. The combination of claim 44 wherein said membrane is made of a translucent polyethylene allowing the transmission of light therethrough.

48. The combination of claim 45 wherein said membrane will transmit therethrough light having a wavelength between 400 and 750 nanometers.

49. An integument pack for the micropropagation of plant tissue in a tissue culturing medium, comprising:
adjacent sheets of single layered high density polyethylene film;
said sheets being heat sealed together along the entire length thereof at a plurality of predetermined locations to form a plurality of cellules;
said cellules each having an open end adapted to receive plant tissue and tissue culturing medium;
said film being heat sealable for closing said open end and being autoclavable so as not to melt, distend, or distort;
said film being pliant and collapsible such that said cellules are flat and can be rolled;
said film being permeable to oxygen and carbon dioxide, having a water vapor transmission rate comparable to that of high density polyethylene, and impermeable to liquids; and
said film being translucent such that light can pass through the integument pack.

50. The integument pack of claim 49 wherein said cellules are made of Chevron 9650 film.

51. The integument pack of claim 49 wherein said open end includes a flap for heat sealing said cellules and suspending the integument pack.

52. The integument pack of claim 51 wherein the integument pack is disposable.

53. The integument pack of claim 49 wherein six individual cellules are formed.

54. The integument pack of claim 49 wherein the integument pack has dimensions of 12 inches wide and 6 inches high.

55. The integument pack of claim 49 wherein said film has a permeability to water vapor of 0.32 grams per 100 square inches per 24 hours.

56. The integument pack of claim 49 wherein said film has interstices no greater than 0.01 micrometers in size but great enough for gas exchange.

57. An apparatus for growing plant tissue in the atmospheric ambient environment, comprising:
a tissue culturing medium for the plant tissue;
a container for receiving and enclosing the plant tissue and tissue culturing medium;
said container being completely sealed around the plant tissue for preventing the exposure of the plant tissue to biological contaminants in the atmospheric ambient environment;
said container being made entirely of a pliable and collapsible material surrounding the plant tissue;
said material being permeable to gases, impermeable to liquids, and translucent to light;
said material having interstices smaller than a virus but large enough for gas exchange;
said container permitting gas exchange and light transmission over its entire surface area;
said container being sterilizable so as not to melt, distend, or distort; and
said container allowing all parts of the plant tissue to be exposed to gas exchanged and light transmitted through the material.

58. A method for growing plant tissue in a disposable cellule in an atmospheric ambient environment, comprising the steps of:
providing a pliable cellule made entirely of a high density polyethylene film which is impermeable to liquids;
inserting a tissue culturing medium into the cellule such that the tissue culturing medium contacts the inner surface of the polyethylene film;
sterilizing the cellule containing tissue culturing medium;
inserting and enclosing plant tissue within the cellule;
sealing the plant tissue completely within the cellule to protect the plant tissue from the biological contaminants in the atmospheric ambient environment;
allowing the gas mixture and pressure within the cellule and the gas mixture and pressure around the cellule in the ambient environment to equalize by gas exchange through said film;
exposing all parts of the plant tissue to light transmitted through the entire cellule to all parts of the plant tissue;
allowing the light to pass completely through the cellule except for any light blocked by the plant tissue and tissue culturing medium; and
diffusing oxygen and carbon dioxide through the cellule to and from all parts of the plant tissue.

59. A method of micropropagation comprising the steps of:
providing a pliable cellule made entirely of a high density polyethylene film which is impermeable to liquids;
placing a tissue culturing medium which is suitable for establishing an initial culture into the cellule;
sterilizing the cellule containing the tissue culturing medium in an autoclave;
placing a plant tissue within the cellule and sealing the plant tissue and tissue culturing medium completely within the cellule to protect the plant tissue from biological contaminants in an ambient environment similar to that of a greenhouse;
exposing all parts of the plant tissue to light transmission and gas exchange through the entire surface of the cellule;
establishing an initial culture of plant tissue;
transferring a portion of the plant tissue from the initial culture to a second cellule having a tissue culturing medium for multiplication therein and disposing of the first cellule;
exposing all parts of the plant tissue to light transmission and gas exchange through the entire surface of the cellule;
multiplying the transferred portion of the plant tissue into a mass of plant tissue;
transferring a portion of the mass of plant tissue to a third cellule having therein a tissue culturing medium suitable for individual plant formation;
exposing all parts of the plant tissue to light transmission and gas exchange through the entire surface of the cellule; and
removing the plant tissue upon plant formation.

* * * * *

UNITED STATES PATENT AND TRADEMARK OFFICE
CERTIFICATE OF CORRECTION

PATENT NO. : 4,908,315

DATED : March 13, 1990

INVENTOR(S) : Malcolm G. Kertz

It is certified that error appears in the above—identified patent and that said Letters Patent is hereby corrected as shown below:

Column 1, line 20; after "cultivar" insert -.- (a period).

Column 6, line 23; delete "sipped" and insert -shipped-.

Column 16, line 7; after "1.25 mil" insert -s-.

Column 22, lines 33 and 34; delete "the contamination rate using the inventive Table 1 compares" and insert -Table 1 compares the contamination rate using the inventive-.

Column 22, line 53; before "59" insert -z-.

Column 23, lines 12 and 42; delete "cert air" and insert -certain-.

Column 24, line 17; after "Stage 1" insert -,-.

Column 24, line 56; delete "stErile" and insert -sterile-.

UNITED STATES PATENT AND TRADEMARK OFFICE
CERTIFICATE OF CORRECTION

PATENT NO. : 4,908,315

DATED : March 13, 1990

INVENTOR(S) : Malcolm G. Kertz

It is certified that error appears in the above-identified patent and that said Letters Patent is hereby corrected as shown below:

Column 25, line 17; delete "5mml" and insert -5 ml-.

Column 26, line 21; after "F" delete -.-.

Column 31, line 35; delete "prevent" and insert -permit-.

Signed and Sealed this

Eighth Day of October, 1991

*Attest:*

HARRY F. MANBECK, JR.

*Attesting Officer*      *Commissioner of Patents and Trademarks*